(12) United States Patent
Dunkel et al.

(10) Patent No.: US 7,847,108 B2
(45) Date of Patent: Dec. 7, 2010

(54) OXATHIIN CARBOXAMIDES

(75) Inventors: Ralf Dunkel, Monheim (DE);
Hans-Ludwig Elbe, Wuppertal (DE);
Heiko Rieck, Ste Foy les Lyon (FR);
Jörg Nico Greul, Leichlingen (DE);
Ulrike Wachendorff-Neumann,
Neuwied (DE); Peter Dahmen, Neuss
(DE); Karl-Heinz Kuck, Langenfeld
(DE); Benoit Hartmann, Langenfeld
(DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 10/544,897

(22) PCT Filed: Feb. 5, 2004

(86) PCT No.: PCT/EP2004/001053

§ 371 (c)(1),
(2), (4) Date: Feb. 2, 2006

(87) PCT Pub. No.: WO2004/072023

PCT Pub. Date: Aug. 26, 2004

(65) Prior Publication Data

US 2007/0004793 A1    Jan. 4, 2007

(30) Foreign Application Priority Data

Feb. 14, 2003  (DE)  ................................. 103 06 244
May 13, 2003  (DE)  ................................. 103 21 270

(51) Int. Cl.
*C07D 327/06* (2006.01)
*A01N 43/32* (2006.01)

(52) U.S. Cl. .......................................... 549/14; 514/433
(58) Field of Classification Search .................. 549/14; 514/433
See application file for complete search history.

(56) References Cited

U.S. PATENT DOCUMENTS

| 3,538,225 | A |   | 11/1970 | Dudarevitch et al. | 424/276 |
|---|---|---|---|---|---|
| 3,657,449 | A |   | 4/1972 | Davis et al. | 424/276 |
| 3,917,592 | A |   | 11/1975 | Kobzina | 260/244 |
| 4,032,573 | A |   | 6/1977 | Kaneko et al. | 260/562 N |
| 4,194,008 | A |   | 3/1980 | Enders et al. | 424/322 |
| 5,223,526 | A |   | 6/1993 | McLoughlin et al. | 514/406 |
| 5,416,103 | A |   | 5/1995 | Eicken et al. | 514/355 |
| 5,438,070 | A |   | 8/1995 | Eicken et al. | 514/403 |
| 5,589,493 | A | * | 12/1996 | Eicken et al. | 514/355 |
| 5,633,218 | A |   | 5/1997 | Spedding et al. | 504/228 |
| 5,914,344 | A |   | 6/1999 | Yoshikawa et al. | 514/406 |
| 5,922,732 | A |   | 7/1999 | Urch et al. | 514/304 |
| 5,965,774 | A |   | 10/1999 | Yoshikawa et al. | 564/305 |
| 5,968,947 | A |   | 10/1999 | Urch et al. | 514/299 |
| 6,093,726 | A |   | 7/2000 | Urch et al. | 514/299 |
| 6,174,894 | B1 |   | 1/2001 | Urch et al. | 514/299 |
| 6,177,442 | B1 |   | 1/2001 | Urch et al. | 514/299 |
| 6,207,676 | B1 |   | 3/2001 | Urch et al. | 514/304 |
| 6,291,474 | B1 |   | 9/2001 | Brightwell et al. | 514/299 |
| 6,391,883 | B1 |   | 5/2002 | Urch et al. | 514/255 |
| 6,573,275 | B1 |   | 6/2003 | Urch et al. | 514/304 |
| 2002/0061913 | A1 |   | 5/2002 | Urch et al. | 514/366 |
| 2004/0039043 | A1 | * | 2/2004 | Elbe et al. | 514/406 |
| 2004/0082572 | A1 |   | 4/2004 | Pineiro et al. | 514/220 |
| 2005/0119130 | A1 |   | 6/2005 | Walter | 504/287 |
| 2005/0203171 | A1 | * | 9/2005 | Rieck et al. | 514/433 |
| 2007/0060579 | A1 | * | 3/2007 | Wachendorff-Neumann et al. | 514/229.2 |

FOREIGN PATENT DOCUMENTS

| CA | 2106497 | 3/1994 |
|---|---|---|
| EP | 0 545 099 | 6/1993 |
| JP | 53-72823 | 6/1978 |
| JP | 8-176112 | 7/1996 |
| JP | 2001-302605 | 10/2001 |

OTHER PUBLICATIONS

Hahn, et al., "Synthesis of Trifluoromethylated Dihydro-1,4-oxathiin-3-carboxanilides Through Polymer-Bound Activated Ester," Heterocycles, vol. 48(11), 1998, pp. 2253-2261.*
Hahn, Hoh-Guy, et al.: "Synthesis of trifluoromethylated dihydro-1,4-oxathiincarboxanilides and their fungicidal activity" Han'Guk Nonghwa Hakoechi, 44(3), 191-196 (2001).*
English Translation of Hahn et al. (J. Korean Soc. Agric. Chem. Biotechnol 44 (3),191-196 (2001)).*
Thornber (Chem. Soc. Rev., 1979, v. 8, p. 563-580).*
Silverman, R. B. (The Org. Chem. of Drug Design and Drug Action, Academic Press, Inc.: San Diego, 1992, pp. 4-51).*
The Merck Index, "Carboxin", Momongraph No. 1837.
Bull. Korean Chem. Soc., vol. 21, No. 2, (month unavailable) 2000, pp. 165-166, Nakcheol Jeong et al, "A Facile Preparation of the Fluoroaryl Zinc Halides: an Application to the Synthesis of Diflunisal".

(Continued)

*Primary Examiner*—Robert Havlin
(74) *Attorney, Agent, or Firm*—Richard E. L. Henderson

(57) ABSTRACT

This invention relates to novel oxathiincarboxamides of the formula (I)

(I)

in which $G^1$, $G^2$, $G^3$, n, $R^1$, $R^2$, $R^3$, $R^4$, $R^5$ and Z are as defined in the disclosure,
to a plurality of processes for preparing these compounds and their use for controlling unwanted microorganisms, and to novel intermediates and their preparation.

6 Claims, No Drawings

OTHER PUBLICATIONS

Chem. Pharm. Bull. 40(1), (month unavailable) 1992, pp. 240-244, Kiyoshi Taniguchi et al, "New 2-Aryliminoimidazolidines. II.[1α] Synthesis and Antihypertensive Activity of 2-(Biphenylimino)-imidazolidines".

Heterocycles, vol. 29, No. 6, (month unavailable) 1989, pp. 1013-1016, Yoshinori Kondo et al, "Palladium-Catalyzed Indole and Benzofuran Ring Formation Accompanying Carbonylation".

J. Med. Chem., 39, (month unavailable) 1996, pp. 892-903, Lee F. Kuyper et al, "High-Affinity Inhibitors of Dihydrofolate Reductase: Antimicrobial and Anticaner Activities of 7,8-Dialkyl-1,3-diaminopyrrolo[3,2-f]quinazolines with Small Molecular Size".

Synthesis, Jun. 1995, pp. 713-716, Michael Harmata et al, "A General, Regioselective Synthesis of 2-Alkenylanilines".

Synth. Commun., 24 (2), (month unavailable) 1994, pp. 267-272, Maryam Hojjat et al, "An Activated Trifluoromethyl Group as a Novel Synthon for a Substituted Vinly Function: Facile Synthesis of 2-(Substituted 1-Alkenyl)Anilines".

Synthesis, Feb. 1994, pp. 142-144, Michael Harmata et al, "A General, Regioselective Synthesis of 2-Alkylanilines".

J. Am. Chem. Soc., 100:15, Jul. 19, 1978, pp. 4842-4852, Tsutomu Sugasawa et al, "Aminohaloborane in Organic Synthesis. 1. Specific Ortho Substitution Reaction of Anilines".

* cited by examiner

OXATHIIN CARBOXAMIDES

The present patent application has been filed under 35 U.S.C. 371 as a national stage application of PCT/EP2004/001053, filed Feb. 5, 2004, which was published in German as International Patent Publication WO 2004/072023 on Aug. 26, 2004, and is entitled to the right of priority of German Patent Applications 103 06 244.0, filed Feb. 14, 2003, and 103 21 270.1, filed May 13, 2003.

The present invention relates to novel oxathiincarboxamides, to a plurality of processes for their preparation and to their use for controlling unwanted microorganisms.

It is already known that numerous carboxamides have fungicidal properties (cf., for example, EP-A 0 591 699, EP-A 0 545 099, DE-A 16 17 921, JP-A 2001-302605, JP-A 10-251240, JP-A 8-176112, JP-A 53-72823 and U.S. Pat. No. 3,657,449).

Thus, a number of 6-methyl-2,3-dihydro-1,4-oxathiin-5-carboxamides have already been disclosed. N-(4'-Fluoro-1,1'-biphenyl-2-yl)-6-methyl-2,3-dihydro-1,4-oxathiin-5-carboxamide and (6-methyl-(2,3-dihydro-1,4-oxathiin-5-yl))-N-[2-(2-methylpropyl)phenyl]carboxamide from EP-A 0 545 099, (6-methyl-(2,3-dihydro-1,4-oxathiin-5-yl))-N-(2,4,6-trimethyl-phenyl)carboxamide from DE-A 16 17 921, N-[2-(1,3-dimethylbutyl)phenyl](6-methyl-(2,3-dihydro-1,4-oxathiin-5-yl))carboxamide from JP-A 10-251240 and (6-methyl-(2,3-dihydro-1,4-oxathiin-5-yl))-N-(2-methylphenyl)carboxamide from U.S. Pat. No. 3,657,449 may be mentioned by way of example. The activity of these compounds is good; however, in some cases, for example at low application rates, it is unsatisfactory.

This invention now provides novel oxathiincarboxamides of the formula (I)

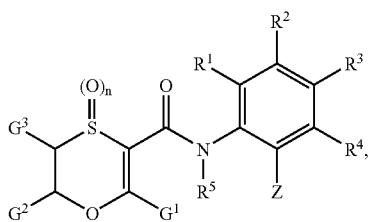

in which $G^1$ represents halogen, trifluoromethyl, difluoromethyl or cyclopropyl, $G^2$ and $G^3$ independently of one another represent hydrogen or methyl, n represents 0, 1 or 2, $R^1$, $R^2$, $R^3$ and $R^4$ independently of one another represent hydrogen, fluorine, chlorine, methyl, isopropyl or methylthio, $R^5$ represents hydrogen, $C_1$-$C_8$-alkyl, $C_1$-$C_6$-alkylsulfinyl, $C_1$-$C_6$-alkylsulfonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylthio, $C_1$-$C_4$-haloalkylsulfinyl, $C_1$-$C_4$-haloalkylsulfonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; ($C_1$-$C_3$-haloalkyl)carbonyl-$C_1$-$C_3$-alkyl, ($C_1$-$C_3$-haloalkoxy)carbonyl-$C_1$-$C_3$-alkyl having in each case 1 to 7 fluorine, chlorine and/or bromine atoms, ($C_1$-$C_3$-alkyl)carbonyl-$C_1$-$C_3$-haloalkyl, ($C_1$-$C_3$-alkoxy)carbonyl-$C_1$-$C_3$-haloalkyl having in each case 1 to 6 fluorine, chlorine and/or bromine atoms, ($C_1$-$C_3$-haloalkyl)carbonyl-$C_1$-$C_3$-haloalkyl, ($C_1$-$C_3$-haloalkoxy)carbonyl-$C_1$-$C_3$-haloalkyl having in each case 1 to 13 fluorine, chlorine and/or bromine atoms; —$COR^6$, —$CONR^7R^8$ or —$CH_2NR^9R^{10}$, $R^6$ represents hydrogen, $C_1$-$C_8$-alkyl, $C_1$-$C_8$-alkoxy, $C_1$-$C_4$-alkoxy-$C_1$-$C_4$-alkyl, $C_3$-$C_8$-cycloalkyl; $C_1$-$C_6$-haloalkyl, $C_1$-$C_6$-haloalkoxy, halo-$C_1$-$C_4$-alkoxy-$C_1$-$C_4$-alkyl, $C_3$-$C_8$-halocycloalkyl having in each case 1 to 9 fluorine, chlorine and/or bromine atoms; —$COR^{11}$, $R^7$ and $R^8$ independently of one another represent hydrogen, $C_1$-$C_8$-alkyl, $C_1$-$C_4$-alkoxy-$C_1$-$C_4$-alkyl, $C_3$-$C_8$-cycloalkyl; $C_1$-$C_8$-haloalkyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms, $R^7$ and $R^8$ furthermore together with the nitrogen atom to which they are attached form a saturated heterocycle having 5 to 8 ring atoms, where the heterocycle may contain 1 or 2 further nonadjacent heteroatoms from the group consisting of oxygen, sulfur and $NR^{12}$ and is optionally mono- or polysubstituted by identical or different substituents from the group consisting of halogen and $C_1$-$C_4$-alkyl, $R^9$ and $R^{10}$ independently of one another represent hydrogen, $C_1$-$C_8$-alkyl, $C_3$-$C_8$-cycloalkyl; $C_1$-$C_8$-haloalkyl, $C_3$-$C_8$-halocycloalkyl having in each case 1 to 9 fluorine, chlorine and/or bromine atoms, $R^9$ and $R^{10}$ furthermore together with the nitrogen atom to which they are attached form a saturated heterocycle having 5 to 8 ring atoms, where the heterocycle may contain 1 or 2 further nonadjacent heteroatoms from the group consisting of oxygen, sulfur and $NR^{12}$ and is optionally mono- or polysubstituted by identical or different substituents from the group consisting of halogen and $C_1$-$C_4$-alkyl, $R^{11}$ represents hydrogen, $C_1$-$C_8$-alkyl, $C_1$-$C_8$-alkoxy, $C_1$-$C_4$-alkoxy-$C_1$-$C_4$-alkyl, $C_3$-$C_8$-cycloalkyl; $C_1$-$C_6$-haloalkyl, $C_1$-$C_6$-haloalkoxy, halo-$C_1$-$C_4$-alkoxy-$C_1$-$C_4$-alkyl, $C_3$-$C_8$-halocycloalkyl having in each case 1 to 9 fluorine, chlorine and/or bromine atoms, $R^{12}$ represents hydrogen or $C_1$-$C_6$-alkyl, Z represents $Z^1$, $Z^2$, $Z^3$ or $Z^4$, where $Z^1$ represents phenyl which is optionally mono- to pentasubstituted by identical or different substituents, $Z^2$ represents cycloalkyl or bicycloalkyl which is optionally mono- or polysubstituted by identical or different substituents, $Z^3$ represents unsubstituted $C_2$-$C_{20}$-alkyl or represents $C_1$-$C_{20}$-alkyl which is mono- or polysubstituted by identical or different substituents from the group consisting of halogen and $C_3$-$C_6$-cycloalkyl, where the cycloalkyl moiety for its part may optionally be mono- or polysubstituted by identical or different substituents from the group consisting of halogen and $C_1$-$C_4$-alkyl, $Z^4$ represents $C_2$-$C_{20}$-alkenyl or $C_2$-$C_{20}$-alkynyl which is in each case optionally mono- or polysubstituted by identical or different substituents from the group consisting of halogen and $C_3$-$C_6$-cycloalkyl, where the cycloalkyl moiety for its part may optionally be mono- or polysubstituted by identical or different substituents from the group consisting of halogen and $C_1$-$C_4$-alkyl, or $R^1$, $R^2$ and $R^3$ independently of one another represent hydrogen or fluorine and Z and $R^4$ together with the carbon atoms to which they are attached form an optionally substituted 5- or 6-membered carbocyclic or heterocyclic ring.

Furthermore, it has been found that oxathiincarboxamides of the formula (I) are obtained when a) oxathiincarboxylic acid derivatives of the formula (II)

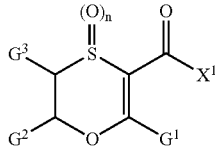

(II)

in which
$G^1$, $G^2$, $G^3$ and n are as defined above,
$X^1$ represents halogen or hydroxyl,
are reacted with aniline derivatives of the formula (III)

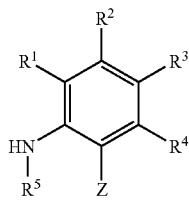

(III)

in which
$R^1$, $R^2$, $R^3$, $R^4$, $R^5$ and Z are as defined above,
if appropriate in the presence of a catalyst, if appropriate in the presence of a condensing agent, if appropriate in the presence of an acid binder and if appropriate in the presence of a diluent, or b) halooxathiincarboxamides of the formula (IV)

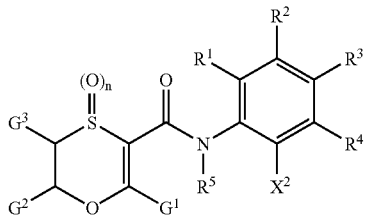

(IV)

in which
$G^1$, $G^2$, $G^3$, n, $R^1$, $R^2$, $R^3$, $R^4$ and $R^5$ are as defined above,
$X^2$ represents bromine or iodine,
are reacted with boronic acid derivatives of the formula (V)

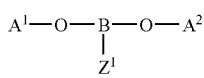

(V)

in which
$Z^1$ is as defined above and
$A^1$ and $A^2$ each represent hydrogen or together represent tetramethylethylene,
in the presence of a catalyst, if appropriate in the presence of an acid binder and if appropriate in the presence of a diluent, or c) oxathiincarboxamide boronic acid derivatives of the formula (VI)

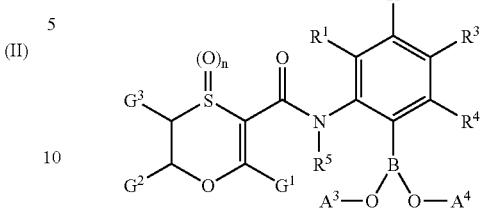

(VI)

in which
$G^1$, $G^2$, $G^3$, n, $R^1$, $R^2$, $R^3$, $R^4$ and $R^5$ are as defined above,
$A^3$ and $A^4$ each represent hydrogen or together represent tetramethylethylene,
are reacted with phenyl derivatives of the formula (VII)

$X^3$-$Z^1$ (VII)

in which
$Z^1$ is as defined above and
$X^3$ represents chlorine, bromine, iodine or trifluoromethylsulfonate,
in the presence of a catalyst, if appropriate in the presence of an acid binder and if appropriate in the presence of a diluent, or d) halooxathiincarboxamides of the formula (IV)

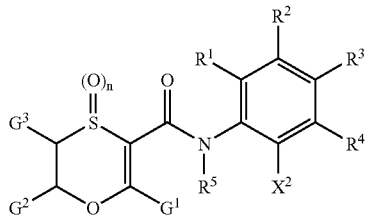

(IV)

in which
$G^1$, $G^2$, $G^3$, n, $R^1$, $R^2$, $R^3$, $R^4$ and $R^5$ are as defined above,
$X^2$ represents bromine or iodine,
are reacted with phenyl derivatives of the formula (VII)

$X^3$-$Z^1$ (VII)

in which
$Z^1$ is as defined above and
$X^3$ represents chlorine, bromine, iodine or trifluoromethylsulfonate,
in the presence of a palladium or nickel catalyst and in the presence of 4,4,4',4',5,5,5',5'-octamethyl-2,2'-bis-1,3,2-dioxaborolane, if appropriate in the presence of an acid binder and if appropriate in the presence of a diluent, or e) oxathiincarboxamides of the formula (Ia)

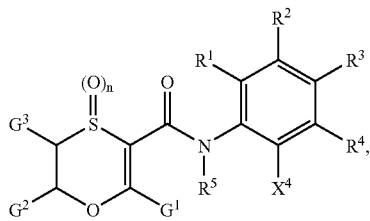

(Ia)

in which
$G^1$, $G^2$, $G^3$, n, $R^1$, $R^2$, $R^3$, $R^4$ and $R^5$ are as defined above,
$X^4$ represents $C_2$-$C_{20}$-alkenyl or $C_2$-$C_{20}$-alkynyl, each of which is optionally mono- or polysubstituted by identical or different substituents from the group consisting of halogen and $C_3$-$C_6$-cycloalkyl, where the cycloalkyl moiety for its part may optionally be substituted by halogen and/or $C_1$-$C_4$-alkyl, are hydrogenated, if appropriate in the presence of a diluent and if appropriate in the presence of a catalyst, or f) hydroxyalkyloxathiincarboxamides of the formula (VIII)

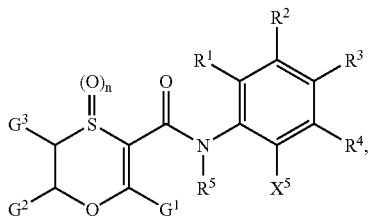

(VIII)

in which $G^1$, $G^2$, $G^3$, n, $R^1$, $R^2$, $R^3$, $R^4$ and $R^5$ are as defined above, $X^5$ represents $C_2$-$C_{20}$-hydroxyalkyl which is optionally additionally mono- or polysubstituted by identical or different substituents from the group consisting of halogen and $C_3$-$C_6$-cycloalkyl, where the cycloalkyl moiety for its part may optionally be substituted by halogen and/or $C_1$-$C_4$-alkyl, are dehydrated, if appropriate in the presence of a diluent and if appropriate in the presence of an acid, or g) halooxathiincarboxamides of the formula (IV)

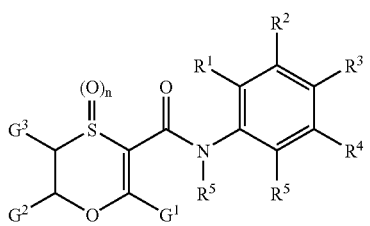

(IV)

in which $G^1$, $G^2$, $G^3$, n, $R^1$, $R^2$, $R^3$, $R^4$ and $R^5$ are as defined above, $X^2$ represents bromine or iodine, are reacted with an alkyne of the formula (IX)

HC≡—$A^5$ (IX), in which $A^5$ represents $C_2$-$C_{18}$-alkyl, each of which is optionally mono- or polysubstituted by identical or different substituents from the group consisting of halogen and $C_3$-$C_6$-cycloalkyl, where the cycloalkyl moiety for its part may optionally be substituted by halogen and/or $C_1$-$C_4$-alkyl, or an alkene of the formula (X)

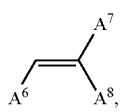

(X)

in which $A^6$, $A^7$ and $A^8$ independently of one another each represent hydrogen or alkyl which is optionally mono- or polysubstituted by identical or different substituents from the group consisting of halogen and $C_3$-$C_6$-cycloalkyl, where the cycloalkyl moiety for its part may optionally be substituted by halogen and/or $C_1$-$C_4$-alkyl and the total number of carbon atoms of the open-chain part of the molecule does not exceed the number 20, if appropriate in the presence of a diluent, if appropriate in the presence of an acid binder and in the presence of one or more catalysts, or h) ketones of the formula (XI)

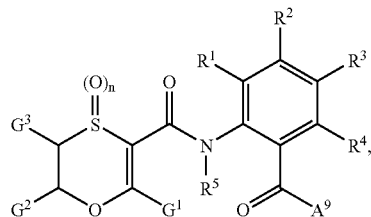

(XI)

in which $G^1$, $G^2$, $G^3$, n, $R^1$, $R^2$, $R^3$, $R^4$ and $R^5$ are as defined above, $A^9$ represents hydrogen or $C_1$-$C_{18}$-alkyl which is optionally mono- or polysubstituted by identical or different substituents from the group consisting of halogen and $C_3$-$C_6$-cycloalkyl, where the cycloalkyl moiety for its part may optionally be substituted by halogen and/or $C_1$-$C_4$-alkyl, are reacted with a phosphorus compound of the formula (XII)

$A^{10}$-Px (XII), in which $A^{10}$ represents $C_1$-$C_{18}$-alkyl which is optionally mono- or polysubstituted by identical or different substituents from the group consisting of halogen and $C_3$-$C_6$-cycloalkyl, where the cycloalkyl moiety for its part may optionally be substituted by halogen and/or $C_1$-$C_4$-alkyl, Px represents a grouping —$P^+(C_6H_5)_3Cl^-$, —$P^+(C_6H_5)_3Br^-$, —$P^+(C_6H_5)_3I^-$, —$P(=O)(OCH_3)_3$ or —$P(=O)(OC_2H_5)_3$, if appropriate in the presence of a diluent, or i) oxathiincarboxamides of the formula (Ib)

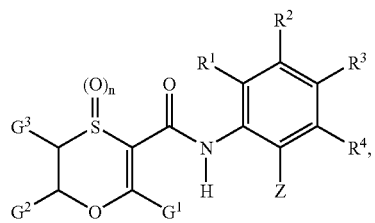

(Ib)

in which $G^1$, $G^2$, $G^3$, n, $R^1$, $R^2$, $R^3$, $R^4$ and Z are as defined above, are reacted with halides of the formula (XIII)

$R^{5-1}$—$X^6$ (XIII)

in which $R^{5-1}$ represents $C_1$-$C_8$-alkyl, $C_1$-$C_6$-alkylsulfinyl, $C_1$-$C_6$-alkylsulfonyl, $C_1$-$C_4$-alkoxy-$C_1$-$C_4$-alkyl, $C_3$-$C_8$-cycloalkyl; $C_1$-$C_6$-haloalkyl, $C_1$-$C_4$-haloalkylthio, $C_1$-$C_4$-haloalkylsulfinyl, $C_1$-$C_4$-haloalkylsulfonyl, halo-$C_1$-$C_4$-alkoxy-$C_1$-$C_4$-alkyl, $C_3$-$C_8$-halocycloalkyl having in each case 1 to 9 fluorine, chlorine and/or bromine atoms, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; ($C_1$-$C_3$-haloalkyl)carbonyl-$C_1$-$C_3$-alkyl, ($C_1$-$C_3$-haloalkoxy)carbonyl-$C_1$-$C_3$-alkyl having in each case 1 to 7 fluorine, chlorine and/or bromine atoms, ($C_1$-$C_3$-alkyl)carbonyl-$C_1$-$C_3$-haloalkyl, ($C_1$-$C_3$-alkoxy)carbonyl-$C_1$-$C_3$-haloalkyl having in each case 1 to 6 fluorine, chlorine and/or bromine atoms, ($C_1$-$C_3$-haloalkyl)carbonyl-$C_1$-$C_3$-haloalkyl, ($C_1$-$C_3$-haloalkoxy)carbonyl-$C_1$-$C_3$-haloalkyl having in each case 1 to 13 fluorine, chlorine and/or bromine atoms; —$COR^6$, —$CONR^7R^8$ or —$CH_2NR^9R^{10}$, $R^6$, $R^7$, $R^8$, $R^9$ and $R^{10}$ are as defined above, $X^6$ represents chlorine, bromine or iodine, in the presence of a base and in the presence of a diluent.

Finally, it has been found that the novel oxathiincarboxamides of the formula (I) have very good microbicidal properties and can be used for controlling unwanted microorganisms both in crop protection and in the protection of materials.

Surprisingly, the oxathiincarboxamides of the formula (I) according to the invention have considerably better fungicidal activity than the constitutionally most similar active compounds of the prior art having the same direction of action.

If appropriate, the compounds according to the invention can be present as mixtures of different possible isomeric forms, in particular of stereoisomers, such as, for example, E and Z, threo and erythro and also optical isomers, and, if appropriate, also of tautomers. What is claimed are both the E and the Z isomers, and the threo and erythro and also the optical isomers, any mixtures of these isomers, and the possible tautomeric forms.

The formula (I) provides a general definition of the oxathiincarboxamides according to the invention. Preferred radical definitions of the formulae mentioned above and below are given below. These definitions apply both to the end products of the formula (I) and, correspondingly, to all intermediates.

$G^1$ preferably represents fluorine, chlorine, bromine, iodine, trifluoromethyl, difluoromethyl or cyclopropyl.

$G^1$ particularly preferably represents chlorine, bromine, iodine, trifluoromethyl, difluoromethyl or cyclopropyl.

$G^1$ very particularly preferably represents trifluoromethyl.

$G^1$ also very particularly preferably represents difluoromethyl.

$G^1$ also very particularly preferably represents cyclopropyl.

$G^2$ preferably represents hydrogen.

$G^2$ also preferably represents methyl.

$G^3$ preferably represents hydrogen.

$G^3$ also preferably represents methyl.

$G^2$ and $G^3$ particularly preferably both represent hydrogen.

n preferably represents 0 or 2.

n particularly preferably represents 0.

n also particularly preferably represents 2.

$R^1$ preferably represents hydrogen, fluorine, chlorine or methyl.

$R^1$ particularly preferably represents hydrogen, fluorine or chlorine.

$R^1$ very particularly preferably represents hydrogen.

$R^1$ also very particularly preferably represents fluorine.

$R^2$ preferably represents hydrogen, fluorine, chlorine, isopropyl or methylthio.

$R^2$ particularly preferably represents hydrogen, fluorine, isopropyl or methylthio.

$R^2$ very particularly preferably represents hydrogen.

$R^3$ preferably represents hydrogen, fluorine, chlorine or methyl.

$R^3$ particularly preferably represents hydrogen or fluorine.

$R^3$ very particularly preferably represents hydrogen.

$R^3$ also very particularly preferably represents fluorine.

$R^4$ preferably represents hydrogen, fluorine, chlorine or methyl.

$R^4$ particularly preferably represents hydrogen or methyl.

$R^4$ very particularly preferably represents hydrogen.

$R^4$ also very particularly preferably represents methyl.

$R^1$, $R^2$, $R^3$ and $R^4$ very particularly preferably all represent hydrogen.

$R^5$ preferably represents hydrogen; $C_1$-$C_6$-alkyl, $C_1$-$C_4$-alkylsulfinyl, $C_1$-$C_4$-alkyl-sulfonyl, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkylthio, $C_1$-$C_4$-haloalkylsulfinyl, $C_1$-$C_4$-haloalkylsulfonyl, halo-$C_1$-$C_3$-alkoxy-$C_1$-$C_3$-alkyl, $C_3$-$C_6$-halocycloalkyl having in each case 1 to 9 fluorine, chlorine and/or bromine atoms, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; ($C_1$-$C_3$-haloalkyl)carbonyl-$C_1$-$C_3$-alkyl, ($C_1$-$C_3$-haloalkoxy)carbonyl-$C_1$-$C_3$-alkyl having in each case 1 to 7 fluorine, chlorine and/or bromine atoms, ($C_1$-$C_3$-alkyl)carbonyl-$C_1$-$C_3$-haloalkyl, ($C_1$-$C_3$-alkoxy)carbonyl-$C_1$-$C_3$-haloalkyl having in each case 1 to 6 fluorine, chlorine and/or bromine atoms, ($C_1$-$C_3$-haloalkyl)carbonyl-$C_1$-$C_3$-haloalkyl, ($C_1$-$C_3$-haloalkoxy)carbonyl-$C_1$-$C_3$-haloalkyl having in each case 1 to 13 fluorine, chlorine and/or bromine atoms; —$COR^6$, —$CONR^7R^8$ or —$CH_2NR^9R^{10}$.

$R^5$ particularly preferably represents hydrogen, methyl, ethyl, n- or isopropyl, n-, iso-, sec- or tert-butyl, pentyl or hexyl, methylsulfinyl, ethylsulfinyl, n- or isopropylsulfinyl, n-, iso-, sec- or tert-butylsulfinyl, methylsulfonyl, ethylsulfonyl, n- or isopropylsulfonyl, n-, iso-, sec- or tert-butylsulfonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylthio, difluorochloromethylthio, trifluoromethylthio, trifluoromethylsulfinyl, trifluoromethyl sulfonyl, trifluoromethoxymethyl, —$CH_2$—CHO, —$CH_2CH_2$—CHO, —$CH_2$—CO—$CH_3$, —$CH_2$—CO—$CH_2CH_3$, —$CH_2$—CO—CH($CH_3$)$_2$, —$CH_2CH_2$—CO—$CH_3$, —$CH_2CH_2$—CO—$CH_2CH_3$, —$CH_2CH_2$—CO—CH($CH_3$)$_2$, —$CH_2$—C(O)O$CH_3$, —$CH_2$—C(O)O$CH_2CH_3$, —$CH_2$—C(O)OCH($CH_3$)$_2$, —$CH_2CH_2$—C(O)O$CH_3$, —$CH_2CH_2$—C(O)O$CH_2CH_3$, —$CH_2CH_2$—C(O)OCH($CH_3$)$_2$, —$CH_2$—CO—$CF_3$, —$CH_2$—CO—$CCl_3$, —$CH_2$—CO—$CH_2CF_3$, —$CH_2$—CO—$CH_2CCl_3$, —$CH_2CH_2$—CO—$CH_2CF_3$, —$CH_2CH_2$—CO—$CH_2CCl_3$, —$CH_2$—C(O)O$CH_2CF_3$, —$CH_2$—C(O)O$CF_2CF_3$, —$CH_2$—C(O)O$CH_2CCl_3$, —$CH_2$—C(O)O$CCl_2CCl_3$, —$CH_2CH_2$—C(O)O$CH_2CF_3$, —$CH_2CH_2$—C(O)O$CF_2CF_3$, —$CH_2CH_2$—C(O)O$CH_2CCl_3$, —$CH_2CH_2$—C(O)O—$CCl_2CCl_3$; —$COR^6$, —$CONR^7R^8$ or —$CH_2NR^9R^{10}$.

$R^5$ very particularly preferably represents hydrogen; methyl, methoxymethyl, —$CH_2$—CHO, —$CH_2CH_2$—CHO, —$CH_2$—CO—$CH_3$, —$CH_2$—CO—$CH_2CH_3$, —$CH_2$—CO—CH($CH_3$)$_2$ or —$COR^6$.

$R^6$ preferably represents hydrogen, $C_1$-$C_6$-alkyl, $C_1$-$C_4$-alkoxy, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkoxy, halo-$C_1$-$C_3$-alkoxy-$C_1$-$C_3$-alkyl, $C_3$-$C_6$-halocycloalkyl having in each case 1 to 9 fluorine, chlorine and/or bromine atoms, —$COR^{11}$.

$R^6$ particularly preferably represents hydrogen, methyl, ethyl, n- or isopropyl, tert-butyl, methoxy, ethoxy, isopropoxy, tert-butoxy, cyclopropyl; trifluoromethyl, trifluoromethoxy, —$COR^{11}$.

$R^6$ very particularly preferably represents hydrogen, —COCH$_3$, —CHO, —COCH$_2$OCH$_3$, —COCO$_2$CH$_3$, —COCO$_2$CH$_2$CH$_3$.

$R^7$ and $R^8$ independently of one another preferably represent hydrogen, $C_1$-$C_6$-alkyl, $C_1$-$C_3$-alkoxy-$C_1$-$C_3$-alkyl, $C_3$-$C_6$-cycloalkyl; $C_1$-$C_4$-haloalkyl, halo-$C_1$-$C_3$-alkoxy-$C_1$-$C_3$-alkyl, $C_3$-$C_6$-halocycloalkyl having in each case 1 to 9 fluorine, chlorine and/or bromine atoms.

$R^7$ and $R^8$ furthermore together with the nitrogen to which they are attached preferably represent a saturated heterocycle having 5 to 8 ring atoms, where the heterocycle may contain 1 or 2 further nonadjacent heteroatoms from the group consisting of oxygen, sulfur and NR$^{12}$ and is optionally mono- to tetrasubstituted by identical or different substituents from the group consisting of halogen and $C_1$-$C_4$-alkyl.

$R^7$ and $R^8$ independently of one another particularly preferably represent hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl.

$R^7$ and $R^8$ furthermore together with the nitrogen atom to which they are attached particularly preferably form a saturated heterocycle from the group consisting of morpholine, thiomorpholine and piperazine, where the piperazine may be substituted at the second nitrogen atom by $R^{12}$, which heterocycle is optionally mono- to tetra-substituted by identical or different substituents from the group consisting of fluorine, chlorine, bromine and methyl.

$R^9$ and $R^{10}$ independently of one another preferably represent hydrogen, $C_1$-$C_6$-alkyl, $C_3$-$C_6$-cycloalkyl; $C_1$-$C_4$-haloalkyl, $C_3$-$C_6$-halocycloalkyl having in each case 1 to 9 fluorine, chlorine and/or bromine atoms.

$R^9$ and $R^{10}$ furthermore together with the nitrogen to which they are attached preferably form a saturated heterocycle having 5 to 8 ring atoms, where the heterocycle may contain 1 or 2 further nonadjacent heteroatoms from the group consisting of oxygen, sulfur and NR$^{12}$ and is optionally mono- or polysubstituted by identical or different substituents from the group consisting of halogen and $C_1$-$C_4$-alkyl.

$R^9$ and $R^{10}$ independently of one another particularly preferably represent hydrogen, methyl, ethyl, n- or isopropyl, n-, iso-, sec- or tert-butyl, methoxymethyl, methoxyethyl, ethoxymethyl, ethoxyethyl, cyclopropyl, cyclopentyl, cyclohexyl; trifluoromethyl, trichloromethyl, trifluoroethyl, trifluoromethoxymethyl.

$R^9$ and $R^{10}$ furthermore together with the nitrogen atom to which they are attached particularly preferably form a saturated heterocycle from the group consisting of morpholine, thiomorpholine and piperazine, where the piperazine may be substituted at the second nitrogen atom by $R^{12}$, which heterocycle is optionally mono- to tetra-substituted by identical or different substituents from the group consisting of fluorine, chlorine, bromine and methyl.

$R^{11}$ preferably represents hydrogen, $C_1$-$C_6$-alkyl, $C_1$-$C_4$-alkoxy, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkoxy, halo-$C_1$-$C_3$-alkoxy-$C_1$-$C_3$-alkyl, $C_3$-$C_6$-halocycloalkyl having in each case 1 to 9 fluorine, chlorine and/or bromine atoms.

$R^{11}$ particularly preferably represents hydrogen, methyl, ethyl, n- or isopropyl, tert-butyl, methoxy, ethoxy, isopropoxy, tert-butoxy, cyclopropyl; trifluoromethyl, trifluoromethoxy.

$R^{12}$ preferably represents hydrogen or $C_1$-$C_4$-alkyl.

$R^{12}$ particularly preferably represents hydrogen, methyl, ethyl, n- or isopropyl, n-, iso-, sec- or tert-butyl.

Z preferably represents Z$^1$.

Z$^1$ preferably represents phenyl which is optionally mono- to pentasubstituted by identical or different substituents, where the substituents are selected from the list W$^1$.

Z$^1$ particularly preferably represents monosubstituted phenyl, where the substituents are selected from the list W$^1$.

Z$^1$ also particularly preferably represents phenyl which is disubstituted by identical or different substituents, where the substituents are selected from the list W$^1$.

Z$^1$ also particularly preferably represents phenyl which is trisubstituted by identical or different substituents, where the substituents are selected from the list W$^1$.

Z$^1$ very particularly preferably represents phenyl which is monosubstituted in the 4-position, where the substituents are selected from the list W$^1$.

Z$^1$ very particularly preferably represents phenyl which is disubstituted by identical or different substituents in the 3,4-position, where the substituents are selected from the list W$^1$.

Z$^1$ very particularly preferably represents phenyl which is disubstituted by identical or different substituents in the 2,4-position, where the substituents are selected from the list W$^1$.

Z$^1$ very particularly preferably represents phenyl which is disubstituted by identical or different substituents in the 3,5-position, where the substituents are selected from the list W$^1$.

Z$^1$ very particularly preferably represents phenyl which is trisubstituted by identical or different substituents in the 2,4,6-position, where the substituents are selected from the list W$^1$.

W$^1$ represents halogen, cyano, nitro, amino, hydroxyl, formyl, carboxyl, carbamoyl, thiocarbamoyl;

in each case straight-chain or branched alkyl, hydroxyalkyl, oxoalkyl, alkoxy, alkoxyalkyl, alkylthioalkyl, dialkoxyalkyl, alkylthio, alkylsulfinyl or alkylsulfonyl having in each case 1 to 8 carbon atoms;

in each case straight-chain or branched alkenyl or alkenyloxy having in each case 2 to 6 carbon atoms;

in each case straight-chain or branched haloalkyl, haloalkoxy, haloalkylthio, haloalkylsulfinyl or haloalkylsulfonyl having in each case 1 to 6 carbon atoms and 1 to 13 identical or different halogen atoms;

in each case straight-chain or branched haloalkenyl or haloalkenyloxy having in each case 2 to 6 carbon atoms and 1 to 11 identical or different halogen atoms;

in each case straight-chain or branched alkylamino, dialkylamino, alkylcarbonyl, alkylcarbonyloxy, alkoxycarbonyl, alkylaminocarbonyl, dialkylaminocarbonyl, arylalkylaminocarbonyl, dialkylaminocarbonyloxy having 1 to 6 carbon atoms in the respective hydrocarbon chains, alkenylcarbonyl or alkynylcarbonyl having 2 to 6 carbon atoms in the respective hydrocarbon chains;

cycloalkyl or cycloalkyloxy having in each case 3 to 6 carbon atoms;

in each case doubly attached alkylene having 3 or 4 carbon atoms, oxyalkylene having 2 or 3 carbon atoms or dioxyalkylene having 1 or 2 carbon atoms, each of which radicals is optionally mono- to tetrasubstituted by identical or different substituents from the group consisting of fluorine, chlorine, oxo, methyl, trifluoromethyl and ethyl;

or a grouping

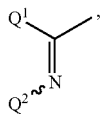

in which
Q¹ represents hydrogen, hydroxyl or alkyl having 1 to 4 carbon atoms, haloalkyl having 1 to 4 carbon atoms and 1 to 9 fluorine, chlorine and/or bromine atoms or cycloalkyl having 1 to 6 carbon atoms and Q² represents hydroxyl, amino, methylamino, phenyl, benzyl or represents in each case optionally cyano-, hydroxyl-, alkoxy-, alkylthio-, alkylamino-, dialkylamino- or phenyl-substituted alkyl or alkoxy having 1 to 4 carbon atoms, or represents alkenyloxy or alkynyloxy having in each case 2 to 4 carbon atoms, and also phenyl, phenoxy, phenylthio, benzoyl, benzoylethenyl, cinnamoyl, heterocyclyl or phenylalkyl, phenylalkyloxy, phenylalkylthio or heterocyclylalkyl having in each case 1 to 3 carbon atoms in the respective alkyl moieties, each of which radicals is optionally mono- to trisubstituted in the cyclic part by halogen and/or straight-chain or branched alkyl or alkoxy having 1 to 4 carbon atoms.

$W^1$ preferably represents fluorine, chlorine, bromine, methyl, ethyl, n- or i-propyl, n-, i-, s- or t-butyl, methoxy, ethoxy, n- or i-propoxy, trifluoromethyl, trifluoroethyl, difluoromethoxy, trifluoromethoxy, difluorochloromethoxy, trifluoroethoxy, in each case doubly attached difluoromethylenedioxy or tetrafluoroethylenedioxy,
or a grouping

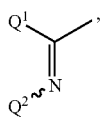

where
Q¹ represents hydrogen, methyl, ethyl or trifluoromethyl and
Q² represents hydroxyl, methoxy, ethoxy, propoxy or isopropoxy.

Z also preferably represents $Z^2$.

$Z^2$ preferably represents cycloalkyl or bicycloalkyl having in each case 3 to 10 carbon atoms, each of which radicals is optionally mono- to tetrasubstituted by identical or different substituents from the group consisting of halogen and $C_1$-$C_4$-alkyl.

$Z^2$ particularly preferably represents cyclopropyl, cyclopentyl, cyclohexyl, cycloheptyl, cyclooctyl, cyclononyl, bicyclo[2.2.1]heptyl or bicyclo[2.2.2]octyl, each of which is optionally mono- to tetrasubstituted by identical or different substituents from the group consisting of chlorine and methyl.

$Z^2$ very particularly preferably represents cyclopropyl which is substituted by chlorine and methyl.

Z also preferably represents $Z^3$.

$Z^3$ preferably represents unsubstituted $C_2$-$C_{20}$-alkyl or represents $C_1$-$C_{20}$-alkyl which is mono- or polysubstituted by identical or different substituents from the group consisting of fluorine, chlorine, bromine, iodine and $C_3$-$C_6$-cycloalkyl, where the cycloalkyl moiety for its part may be mono- to tetrasubstituted by identical or different substituents from the group consisting of fluorine, chlorine, bromine, iodine, $C_1$-$C_4$-alkyl and $C_1$-$C_4$-haloalkyl.

$Z^3$ particularly preferably represents unsubstituted $C_2$-$C_{20}$-alkyl.

$Z^3$ also particularly preferably represents $C_1$-$C_{20}$-alkyl which is substituted by chlorine, cyclopropyl, dichlorocyclopropyl, cyclobutyl, cyclopentyl or cyclohexyl.

Z also preferably represents $Z^4$.

$Z^4$ preferably represents $C_2$-$C_{20}$-alkenyl or $C_2$-$C_{20}$-alkynyl, each of which is optionally mono- or polysubstituted by identical or different substituents from the group consisting of fluorine, chlorine, bromine, iodine and $C_3$-$C_6$-cycloalkyl, where the cycloalkyl moiety for its part may optionally be mono- to tetrasubstituted by identical or different substituents from the group consisting of fluorine, chlorine, bromine, iodine, $C_1$-$C_4$-alkyl and $C_1$-$C_4$-haloalkyl.

$Z^4$ particularly preferably represents $C_2$-$C_{20}$-alkenyl or $C_2$-$C_{20}$-alkynyl.

Z and $R^4$ also preferably together with the carbon atoms to which they are attached represent a 5- or 6-membered carbocyclic or heterocyclic ring which is optionally mono- to tetrasubstituted by identical or different substituents.

Z and $R^4$ also particularly preferably together with the carbon atoms to which they are attached represent a 5- or 6-membered carbocyclic ring which is optionally mono-, di- or trisubstituted by methyl.

Preferred are those compounds of the formula (I) in which all radicals each have the preferred meanings mentioned above.

Particular preference is given to those compounds of the formula (I) in which all radicals each have the particularly preferred meanings mentioned above.

Preference is furthermore given to compounds of the formula (Ic)

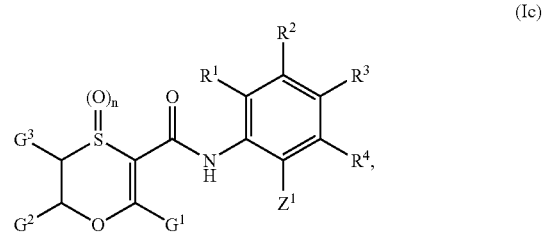

in which
$G^1$, $G^2$, $G^3$, n, $R^1$, $R^2$, $R^3$, $R^4$ and $Z^1$ are as defined above.

Particular preference is given to compounds of the formula (Ic) in which $G^1$ represents trifluoromethyl.

Particular preference is given to compounds of the formula (Ic) in which $G^1$ represents difluoromethyl.

Particular preference is given to compounds of the formula (Ic) in which $R^1$, $R^2$, $R^3$ and $R^4$ each represent hydrogen.

Particular preference is given to compounds of the formula (Ic) in which n represents 0.

Preference is furthermore given to compounds of the formula (Id)

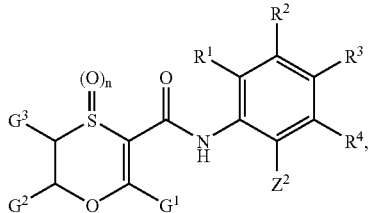

(Id)

in which
$G^1$, $G^2$, $G^3$, n, $R^1$, $R^2$, $R^3$, $R^4$ and $Z^2$ are as defined above.

Particular preference is given to compounds of the formula (Id) in which $G^1$ represents trifluoromethyl.

Particular preference is given to compounds of the formula (Id) in which $G^1$ represents difluoromethyl.

Particular preference is given to compounds of the formula (Id) in which $R^1$, $R^2$, $R^3$ and $R^4$ each represent hydrogen.

Particular preference is given to compounds of the formula (Id) in which n represents 0.

Preference is furthermore given to compounds of the formula (Ie)

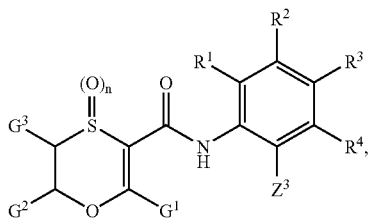

(Ie)

in which
$G^1$, $G^2$, $G^3$, n, $R^1$, $R^2$, $R^3$, $R^4$ and $Z^3$ are as defined above.

Particular preference is given to compounds of the formula (Ie) in which $G^1$ represents trifluoromethyl.

Particular preference is given to compounds of the formula (Ie) in which $G^1$ represents difluoromethyl.

Particular preference is given to compounds of the formula (Ie) in which $R^1$, $R^2$, $R^3$ and $R^4$ each represent hydrogen.

Particular preference is given to compounds of the formula (Ie) in which n represents 0.

Preference is furthermore given to compounds of the formula (If)

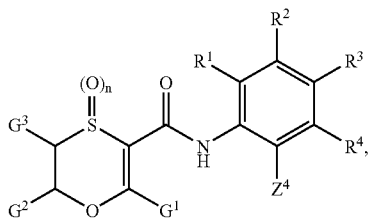

(If)

in which
$G^1$, $G^2$, $G^3$, n, $R^1$, $R^2$, $R^3$, $R^4$ and $Z^4$ are as defined above.

Particular preference is given to compounds of the formula (If) in which $G^1$ represents trifluoromethyl.

Particular preference is given to compounds of the formula (If) in which $G^1$ represents difluoromethyl.

Particular preference is given to compounds of the formula (If) in which $R^1$, $R^2$, $R^3$ and $R^4$ each represent hydrogen.

Particular preference is given to compounds of the formula (If) in which n represents 0.

Preference is furthermore given to compounds of the formula (Ig)

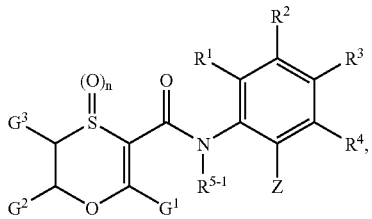

(Ig)

in which
$G^1$, $G^2$, $G^3$, n, $R^1$, $R^2$, $R^3$, $R^4$, $R^{5-1}$ and Z are as defined above.

$R^{5-1}$ preferably represents $C_1$-$C_6$-alkyl, $C_1$-$C_4$-alkylsulfinyl, $C_1$-$C_4$-alkylsulfonyl, $C_1$-$C_3$-alkoxy-$C_1$-$C_3$-alkyl, $C_3$-$C_6$-cycloalkyl; $C_1$-$C_4$-haloalkyl, $C_1$-$C_4$-haloalkylthio, $C_1$-$C_4$-haloalkylsulfinyl, $C_1$-$C_4$-haloalkylsulfonyl, halo-$C_1$-$C_3$-alkoxy-$C_1$-$C_3$-alkyl, $C_3$-$C_6$-halocycloalkyl having in each case 1 to 9 fluorine, chlorine and/or bromine atoms, formyl-$C_1$-$C_3$-alkyl, ($C_1$-$C_3$-alkyl)carbonyl-$C_1$-$C_3$-alkyl, ($C_1$-$C_3$-alkoxy)carbonyl-$C_1$-$C_3$-alkyl; ($C_1$-$C_3$-haloalkyl)carbonyl-$C_1$-$C_3$-alkyl, ($C_1$-$C_3$-haloalkoxy)carbonyl-$C_1$-$C_3$-alkyl having in each case 1 to 7 fluorine, chlorine and/or bromine atoms, ($C_1$-$C_3$-alkyl)carbonyl-$C_1$-$C_3$-haloalkyl, ($C_1$-$C_3$-alkoxy)carbonyl-$C_1$-$C_3$-haloalkyl having in each case 1 to 6 fluorine, chlorine and/or bromine atoms, ($C_1$-$C_3$-haloalkyl)carbonyl-$C_1$-$C_3$-haloalkyl, ($C_1$-$C_3$-haloalkoxy)carbonyl-$C_1$-$C_3$-haloalkyl having in each case 1 to 13 fluorine, chlorine and/or bromine atoms; —$COR^6$, —$CONR^7R^8$ or —$CH_2NR^9R^{10}$.

$R^{5-1}$ particularly preferably represents methyl, ethyl, n- or isopropyl, n-, iso-, sec- or tert-butyl, pentyl or hexyl, methylsulfinyl, ethylsulfinyl, n- or isopropylsulfinyl, n-, iso-, sec- or tert-butylsulfinyl, methylsulfonyl, ethylsulfonyl, n- or isopropylsulfonyl, n-, iso-, sec- or tert-butylsulfonyl, methoxymethyl, methoxyethyl, ethoxymethyl, ethoxyethyl, cyclopropyl, cyclopentyl, cyclohexyl, trifluoromethyl, trichloromethyl, trifluoroethyl, difluoromethylthio, difluorochloromethylthio, trifluoromethylthio, trifluoromethylsulfinyl, trifluoromethylsulfonyl, trifluoromethoxymethyl, —$CH_2$—CHO, —$CH_2CH_2$—CHO, —$CH_2$—CO—$CH_3$, —$CH_2$—CO—$CH_2CH_3$, —$CH_2$—CO—CH($CH_3$)$_2$, —$CH_2CH_2$—CO—$CH_3$, —$CH_2CH_2$—CO—$CH_2CH_3$, —$CH_2CH_2$—CO—CH($CH_3$)$_2$, —$CH_2$—C(O)$OCH_3$, —$CH_2$—C(O)$OCH_2CH_3$, —$CH_2$—C(O)OCH($CH_3$)$_2$, —$CH_2CH_2$—C(O)$OCH_3$, —$CH_2CH_2$—C(O)$OCH_2CH_3$, —$CH_2CH_2$—C(O)OCH($CH_3$)$_2$, —$CH_2$—CO—$CF_3$, —$CH_2$—CO—$CCl_3$, —$CH_2$—CO—$CH_2CF_3$, —$CH_2$—CO—$CH_2CCl_3$, —$CH_2CH_2$—CO—$CH_2CF_3$, —$CH_2CH_2$—CO—$CH_2CCl_3$, —$CH_2$—C(O)$OCH_2CF_3$, —$CH_2$—C(O)$OCF_2CF_3$, —$CH_2$—C(O)$OCH_2CCl_3$, —$CH_2$—C(O)$OCCl_2CCl_3$, —$CH_2CH_2$—C(O)$OCH_2CF_3$, —$CH_2CH_2$—C(O)$OCF_2CF_3$, —$CH_2CH_2$—C(O)$OCH_2CCl_3$, —$CH_2CH_2$—C(O)O—$CCl_2CCl_3$; —$COR^6$, —$CONR^7R^8$ or —$CH_2NR^9R^{10}$.

$R^{5-1}$ very particularly preferably represents methyl, methoxymethyl, —CH$_2$—CHO, —CH$_2$CH$_2$—CHO, —CH$_2$—CO—CH$_3$, —CH$_2$—CO—CH$_2$CH$_3$, —CH$_2$—CO—CH(CH$_3$)$_2$ or —COR$^6$.

Particular preference is given to compounds of the formula (Ig) in which G$^1$ represents trifluoromethyl.

Particular preference is given to compounds of the formula (Ig) in which G$^1$ represents difluoromethyl.

Particular preference is given to compounds of the formula (Ig) in which R$^1$, R$^2$, R$^3$ and R$^4$ each represent hydrogen.

Particular preference is given to compounds of the formula (Ig) in which n represents 0.

Saturated or unsaturated hydrocarbon radicals, such as alkyl or alkenyl, can in each case be straight-chain or branched as far as this is possible, including in combination with heteroatoms, such as, for example, in alkoxy.

The definition C$_1$-C$_{20}$-alkyl embraces the widest range defined here for an alkyl radical. Specifically, this definition includes the meanings methyl, ethyl, n-, isopropyl, n-, iso-, sec-, tert-butyl, and in each case all isomeric pentyls, hexyls, heptyls, octyls, nonyls, decyls, undecyls, dodecyls, tridecyls, tetradecyls, pentadecyls, hexadecyls, heptadecyls, octadecyls, nonadecyls and eicosyls.

The definition C$_2$-C$_{20}$-alkenyl embraces the widest range defined here for an alkenyl radical. Specifically, this definition includes the meanings ethenyl, n-, isopropenyl, n-, iso-, sec-, tert-butenyl, and in each case all isomeric pentenyls, hexenyls, heptenyls, octenyls, nonenyls, decenyls, undecenyls, dodecenyls, tridecenyls, tetradecenyls, pentadecenyls, hexadecenyls, heptadecenyls, octadecenyls, nonadecenyls and eicosenyls.

The definition C$_2$-C$_{20}$-alkynyl embraces the widest range defined here for an alkynyl radical. Specifically, this definition includes the meanings ethynyl, n-, isopropynyl, n-, iso-, sec-, tert-butynyl, and in each case all isomeric pentynyls, hexynyls, heptynyls, octynyls, nonynyls, decynyls, undecynyls, dodecynyls, tridecynyls, tetradecynyls, pentadecynyls, hexadecynyls, heptadecynyls, octadecynyls, nonadecynyls and eicosynyls.

Optionally substituted radicals may be mono- or polysubstituted, where in the case of polysubstitution the substituents can be identical or different.

Halogen-substituted radicals, such as, for example, haloalkyl, are mono- or polyhalogenated. In the case of polyhalogenation, the halogen atoms can be identical or different. Here, halogen denotes fluorine, chlorine, bromine and iodine, in particular fluorine, chlorine and bromine.

The general or preferred radical definitions or illustrations given above can be combined between the respective ranges and preferred ranges as desired. The definitions apply both to the end products and, correspondingly, to precursors and intermediates.

Explanation of the Processes and Intermediates:

Process (a)

Using 6-trifluoromethyl-2,3-dihydro-1,4-oxathiin-5-carbonyl chloride and 4'-chloro-2'-fluoro-1,1'-biphenyl-2-amine as starting materials, the course of the process (a) according to the invention can be illustrated by the formula scheme below.

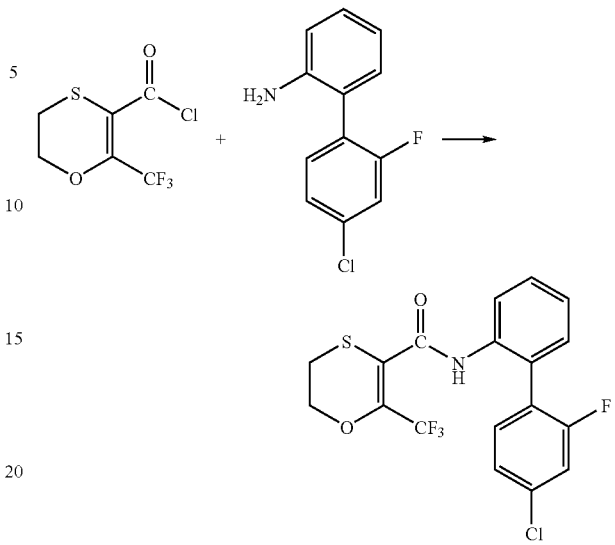

The formula (II) provides a general definition of the oxathiincarboxylic acid derivatives required as starting materials for carrying out the process (a) according to the invention. In this formula (II), G$^1$, G$^2$, G$^3$ and n preferably, particularly preferably and very particularly preferably have those meanings which have already been mentioned in connection with the description of the compounds of the formula (I) according to the invention as being preferred, particularly preferred and very particularly preferred, respectively, for G$^1$, G$^2$, G$^3$ and n. X$^1$ preferably represents chlorine or hydroxyl.

Most of the starting materials of the formula (II) are known, and/or can be prepared by known processes (cf. Han'guk Nonghwa Hakhoechi 2001, 44, 191-196). Novel compounds of the formula (II) and processes for their preparation can be found in the Preparation Examples.

Compounds of the formula (II) in which n represents 1 or 2 are obtained from the corresponding compounds in which n represents 0 by customary oxidation methods, for example by reaction with hydrogen peroxide (H$_2$O$_2$) in the presence of formic acid and a diluent (for example 4-methyl-2-pentanone). The degree of oxidation can in each case be controlled via the reaction conditions.

In the same manner, it is also possible to oxidize compounds of the formula (I) in which n represents 0, giving compounds of the formula (I) in which n represents 1 or 2. The degree of oxidation can in each case be controlled by the reaction conditions.

The formula (III) provides a general definition of the aniline derivatives furthermore required as starting materials for carrying out the process (a) according to the invention. In this formula (III), R$^1$, R$^2$, R$^3$, R$^4$, R$^5$ and Z preferably, particularly preferably and very particularly preferably have those meanings which have already been mentioned in connection with the description of the compounds of the formula (I) according to the invention as being preferred, particularly preferred and very particularly preferred, respectively, for these radicals.

Most of the starting materials of the formula (III) are known, and/or can be prepared by known processes (cf., for example, Bull. Korean Chem. Soc. 2000 21, 165-166; Chem. Pharm. Bull. 1992, 40, 240-244; Heterocycles 1989, 29, 1013-1016; J. Med. Chem. 1996, 39, 892-903; Synthesis 1995, 713-16; Synth. Commun. 1994, 24, 267-272; Synthesis 1994, 142-144; DE-A 27 27 416; EP-A 0 824 099; WO 93/11117, EP-A 0 545 099, EP-A 0 589 301, EP-A 0 589 313 and WO 02/38542).

It is also possible to initially prepare aniline derivatives of the formula (III) in which $R^5$ represents hydrogen and then to derivatize the compounds obtained in this manner using customary methods [for example analogously to the process (i) according to the invention].

Novel compounds of the formula (III) and processes for their preparation can be found in the Preparation Examples.

Process (b)

Using N-(2-bromophenyl)-6-trifluoromethyl-2,3-dihydro-1,4-oxathiin-5-carboxamide and 4-chloro-2-fluorophenylboronic acid as starting materials and a catalyst, the course of the process (b) according to the invention can be illustrated by the formula scheme below.

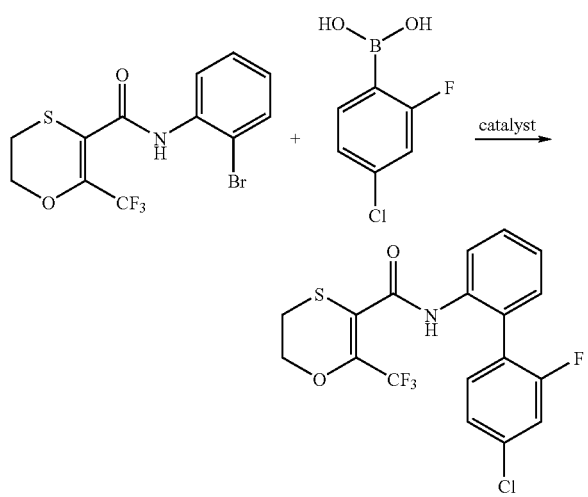

The formula (IV) provides a general definition of the haloxathiincarboxamides required as starting materials for carrying out the process (b) according to the invention. In this formula (IV), $G^1$, $G^2$, $G^3$, n, $R^1$, $R^2$, $R^3$, $R^4$ and $R^5$ preferably, particularly preferably and very particularly preferably have those meanings which have already been mentioned in connection with the description of the compounds of the formula (I) according to the invention as being preferred, particularly preferred and very particularly preferred, respectively, for these radicals and this index. $X^2$ represents bromine or iodine.

The haloxathiincarboxamides of the formula (IV) have hitherto not been disclosed. As novel chemical compounds, they also form part of the subject-matter of the present application. They are obtained when j) oxathiincarboxylic acid derivatives of the formula (II)

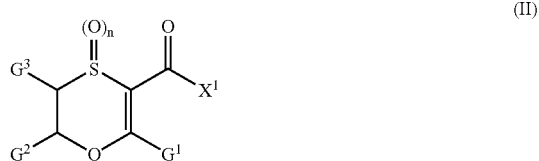

in which
$G^1$, $G^2$, $G^3$ and n are as defined above and
$X^1$ represents halogen or hydroxyl, are reacted with haloanilines of the formula (XIV)

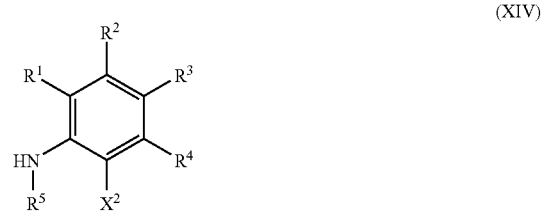

in which
$R^1$, $R^2$, $R^3$, $R^4$, $R^5$ and $X^2$ are as defined above,
if appropriate in the presence of a catalyst, if appropriate in the presence of a condensing agent, if appropriate in the presence of an acid binder and if appropriate in the presence of a diluent.

Process (j)

Using 6-trifluoromethyl-2,3-dihydro-1,4-oxathiin-5-carbonyl chloride and 2-bromoaniline as starting materials, the course of the process (j) according to the invention can be illustrated by the formula scheme below.

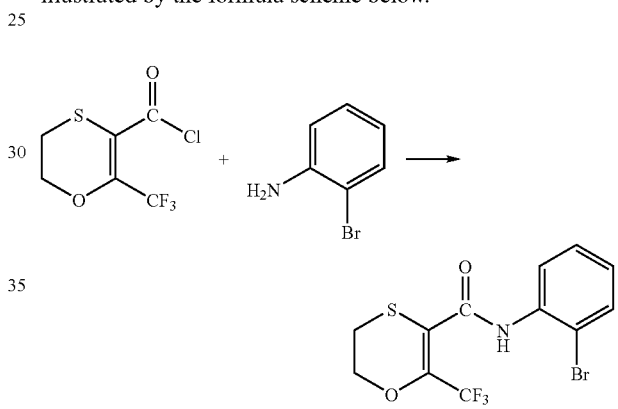

The oxathiincarbonyl halides of the formula (II) required as starting materials for carrying out the process (j) according to the invention have already been described further above, in connection with the process (a) according to the invention.

The formula (XIV) provides a general definition of the haloanilines furthermore required as starting materials for carrying out the process (j) according to the invention. In this formula (XIV), $R^1$, $R^2$, $R^3$, $R^4$, $R^5$ and $X^2$ preferably, particularly preferably and very particularly preferably have those meanings which have already been mentioned in connection with the description of the compounds of the formula (I) according to the invention or of the precursors of the formula (III) as being preferred, particularly preferred and very particularly preferred, respectively, for these radicals.

The haloanilines of the formula (XIV) are commercial chemicals for synthesis or can be obtained by known processes. If $R^5$ does not represent hydrogen, the radical $R^5$ can be introduced at the stage of the compounds of the formula (XIV) using customary derivatization methods. It is also possible to initially prepare compounds of the formula (IV) in which $R^5$ represents hydrogen and then to derivatize the resulting products by customary methods [cf. the process (i) according to the invention].

The formula (V) provides a general definition of the boronic acid derivatives furthermore required as starting materials for carrying out the process (b) according to the invention. In this formula (V), $Z^1$ preferably, particularly preferably and very particularly preferably has those meanings which have already been mentioned in connection with the description of the compounds of the formula (I) according to the invention as being preferred, particularly preferred and very particularly preferred, respectively, for $Z^1$. $A^1$ and $A^2$ each represent hydrogen or together represent tetramethylethylene.

The boronic acid derivatives of the formula (V) are known and/or can be prepared by known processes (cf., for example, WO 01/90084 and U.S. Pat. No. 5,633,218).

Process c)

Using 2-{[6-(trifluoromethyl)-2,3-dihydro-1,4-oxathiin-5-yl]carbonylamino}phenylboronic acid and 1-bromo-4-chloro-2-fluorobenzene as starting materials and a catalyst, the course of the process (c) according to the invention can be illustrated by the formula scheme below.

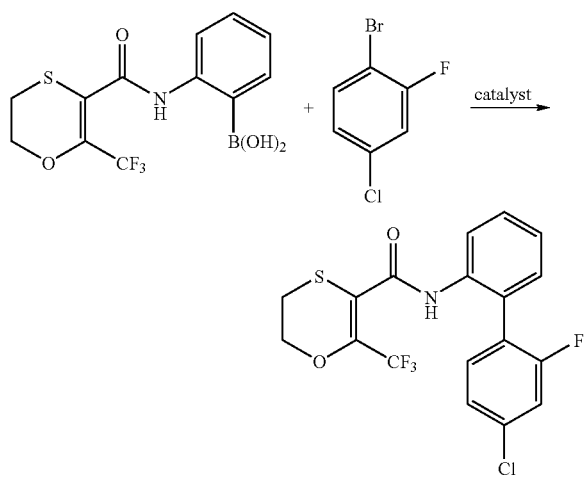

The formula (VI) provides a general definition of the oxathiincarboxamideboronic acid derivatives required as starting materials for carrying out the process (c) according to the invention. In this formula (VI), $G^1$, $G^2$, $G^3$, n, $R^1$, $R^2$, $R^3$, $R^4$ and $R^5$ preferably, particularly preferably and very particularly preferably have those meanings which have already been mentioned in connection with the description of the compounds of the formula (I) according to the invention as being preferred, particularly preferred and very particularly preferred, respectively for these radicals and this index. $A^3$ and $A^4$ each represent hydrogen or together represent tetramethylethylene.

The oxathiincarboxamideboronic acid derivatives of the formula (VI) have hitherto not been disclosed. They are novel chemical compounds and also form part of the subject-matter of the present application. They are obtained when k) an oxathiincarboxylic acid derivative of the formula (II)

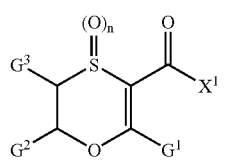

(II)

in which
$G^1$, $G^2$, $G^3$ and n are as defined above and
$X^1$ represents halogen or hydroxyl
is reacted with an anilineboronic acid derivative of the formula (XV)

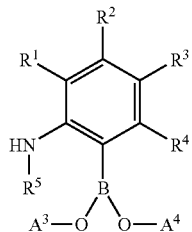

(XV)

in which
$R^1$, $R^2$, $R^3$, $R^4$, $R^5$, $A^3$ and $A^4$ are as defined above,
if appropriate in the presence of a catalyst, if appropriate in the presence of a condensing agent, if appropriate in the presence of an acid binder and if appropriate in the presence of a diluent.

Process (k)

Using 6-trifluoromethyl-2,3-dihydro-1,4-oxathiin-5-carbonyl chloride and 2-amino-phenylboronic acid as starting materials, the course of the process (k) according to the invention can be illustrated by the formula scheme below.

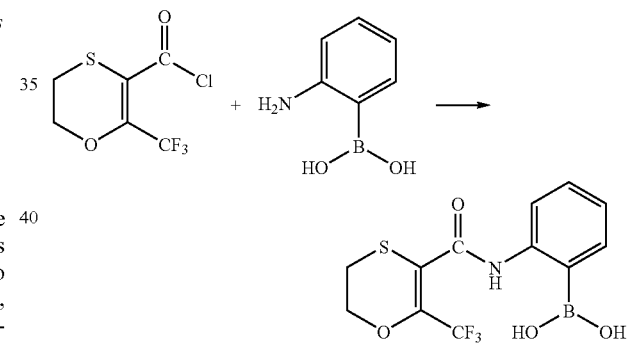

The oxathiincarboxylic acid derivatives of the formula (II) required as starting materials for carrying out the process (k) according to the invention have already been described further above, in connection with the process (a) according to the invention.

The formula (XV) provides a general definition of the anilineboronic acid derivatives furthermore required as starting materials for carrying out the process (k) according to the invention. In this formula (XV), $R^1$, $R^2$, $R^3$, $R^4$ and $R^5$ preferably, particularly preferably and very particularly preferably have those meanings which have already been mentioned in connection with the description of the compounds of the formula (I) according to the invention as being preferred, particularly preferred and very particularly preferred, respectively, for these radicals. $A^3$ and $A^4$ each represent hydrogen or together represent tetramethylethylene.

The anilineboronic acid derivatives of the formula (XV) are known chemicals for synthesis or can be obtained by known processes. If $R^5$ does not represent hydrogen, the radical $R^5$ can be introduced at the stage of the compounds of the formula (XV) using customary derivatization methods. It is also possible to initially prepare compounds of the formula (VI) in which $R^5$ represents hydrogen and then to derivatize the products obtained using customary methods [cf. the process (i) according to the invention].

The formula (VII) provides a general definition of the phenyl derivatives furthermore required as starting materials for carrying out the process (c) according to the invention. In this formula (VII), $Z^1$ preferably, particularly preferably and very particularly preferably has those meanings which have already been mentioned in connection with the description of the compounds of the formula (I) according to the invention as being preferred, particularly preferred and very particularly preferred, respectively, for $Z^1$. $X^3$ represents chlorine, bromine, iodine or trifluoromethylsulfonate.

The phenyl derivatives of the formula (VII) are known chemicals for synthesis.

Process d)

Using N-(2-bromophenyl)-6-trifluoromethyl-2,3-dihydro-1,4-oxathiin-5-carboxamide and 1-bromo-4-chloro-2-fluorobenzene as starting materials and a catalyst and 4,4,4',4',5,5,5',5'-octamethyl-2,2'-bis-1,3,2-dioxaborolane, the course of the process (d) according to the invention can be illustrated by the formula scheme below.

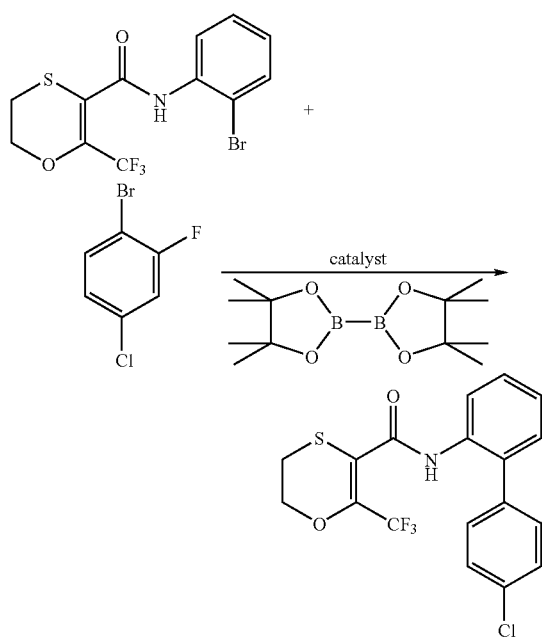

The halooxathiincarboxamides of the formula (IV) and the phenyl derivatives of the formula (VII) required as starting materials for carrying out the process (d) according to the invention have already been described further above, in connection with the processes (b) and (c) according to the invention.

The 4,4,4',4',5,5,5',5'-octamethyl-2,2'-bis-1,3,2-dioxaborolane furthermore required for carrying out the process (d) according to the invention is a commercial chemical for synthesis.

Process e)

If, for example, N-[2-(1,3-dimethylbut-1-enyl)phenyl][6-(trifluoromethyl)(2,3-dihydro-1,4-oxathiin-5-yl)]carboxamide is hydrogenated, the course of the process (e) according to the invention can be illustrated by the formula scheme below.

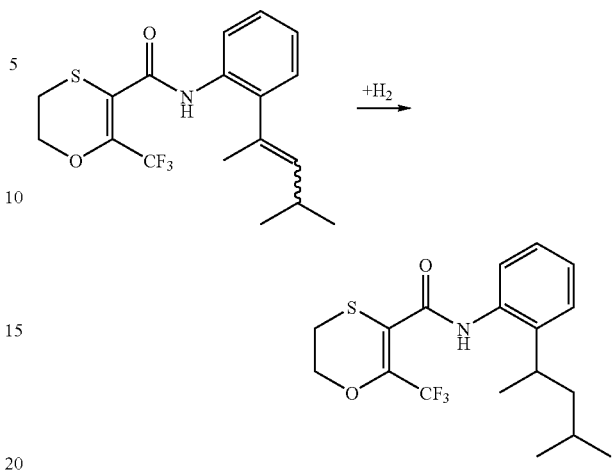

The formula (Ia) provides a general definition of the oxathiincarboxamides required as starting materials for carrying out the process (e) according to the invention. In this formula (Ia), $G^1$, $G^2$, $G^3$, n, $R^1$, $R^2$, $R^3$ and $R^4$ preferably, particularly preferably and very particularly preferably have those meanings which have already been mentioned in connection with the description of the compounds of the formula (I) according to the invention as being preferred, particularly preferred and very particularly preferred, respectively, for these radicals and this index.

$X^4$ preferably represents $C_2$-$C_{20}$-alkenyl or $C_2$-$C_{20}$-alkynyl, each of which is optionally mono- or polysubstituted by identical or different substituents from the group consisting of fluorine, chlorine, bromine, iodine and $C_3$-$C_6$-cycloalkyl, where the cycloalkyl moiety for its part may optionally be mono- to tetrasubstituted by identical or different substituents from the group consisting of fluorine, chlorine, bromine, iodine, $C_1$-$C_4$-alkyl and $C_1$-$C_4$-haloalkyl.

$X^4$ particularly preferably represents $C_2$-$C_{20}$-alkenyl or $C_2$-$C_{20}$-alkynyl.

The compounds of the formula (Ia) are compounds according to the invention and can be prepared according to processes (a), (f), (g) or (h).

Process (f)

If, for example, N-[2-(1-hydroxy-1,3-dimethylbutyl)phenyl][6-(trifluoromethyl)(2,3-dihydro-1,4-oxathiin-5-yl)]carboxamide is dehydrated, the course of the process (f) according to the invention can be illustrated by the formula scheme below.

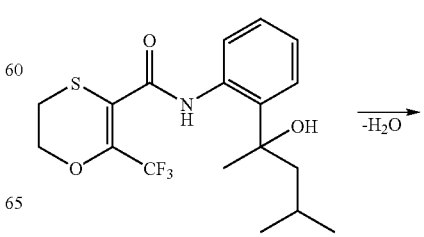

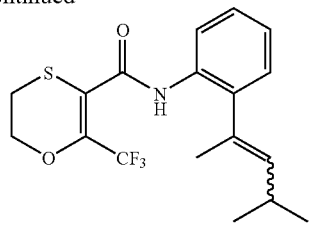

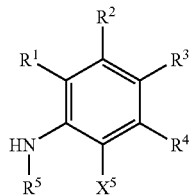

(XVI)

in which
R$^1$, R$^2$, R$^3$, R$^4$, R$^5$ and X$^5$ are as defined above,
if appropriate in the presence of a catalyst, if appropriate in the presence of a condensing agent, if appropriate in the presence of an acid binder and if appropriate in the presence of a diluent.

Process (l)

Using, for example, 6-trifluoromethyl-2,3-dihydro-1,4-oxathiin-5-carbonyl chloride and 2-(2-aminophenyl)-2-heptanol as starting materials, the course of the process (l) according to the invention can be illustrated by the formula scheme below:

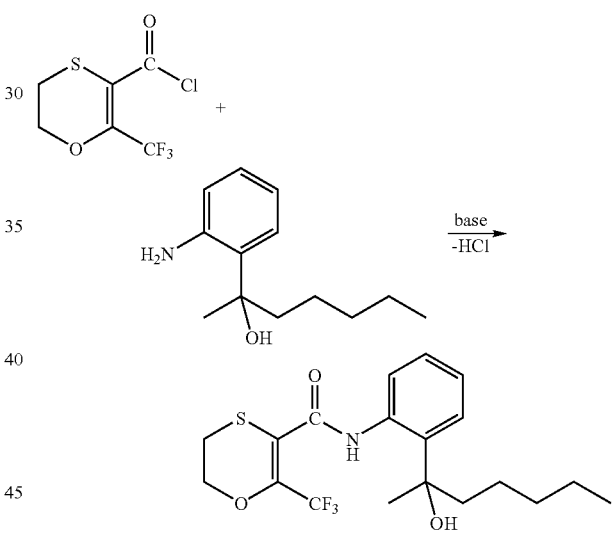

The formula (VIII) provides a general definition of the hydroxyalkyloxathiincarboxamides required as starting materials for carrying out the process (f) according to the invention. In this formula (VIII), G$^1$, G$^2$, G$^3$, n, R$^1$, R$^2$, R$^3$, R$^4$ and R$^5$ preferably, particularly preferably and very particularly preferably have those meanings which have already been mentioned in connection with the description of the compounds of the formula (I) according to the invention as being preferred, particularly preferred and very particularly preferred, respectively, for these radicals and this index.

X$^5$ preferably represents C$_2$-C$_{12}$-hydroxyalkyl which is optionally additionally mono- to tetrasubstituted by identical or different substituents from the group consisting of chlorine, fluorine, bromine and/or C$_3$-C$_6$-cycloalkyl, where the cycloalkyl moiety for its part may optionally be substituted by halogen and/or C$_1$-C$_4$-alkyl.

X$^5$ particularly preferably represents in each case straight-chain or branched hydroxy-ethyl, hydroxypropyl, hydroxybutyl, hydroxypentyl, hydroxyhexyl, hydroxyheptyl, hydroxyoctyl, hydroxynonyl or hydroxydecyl, each of which may be attached in any position and each of which is optionally mono- to tetrasubstituted by identical or different substituents from the group consisting of fluorine, cyclopropyl, difluorocyclopropyl, cyclobutyl, cyclopentyl and cyclohexyl.

The compounds of the formula (VIII) have hitherto not been disclosed and, as novel compounds, also form part of the subject-matter of the present application.

It has also been found that the hydroxyalkylpyrazolylcarboxamides of the formula (VIII) have very good microbicidal properties and can be used for controlling unwanted microorganisms both in crop protection and in the protection of materials.

The hydroxyalkylpyrazolylcarboxamides of the formula (VIII) are obtained when l) oxathiincarboxylic acid derivatives of the formula (II)

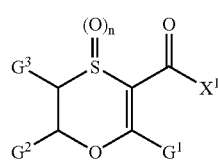

(II)

in which
G$^1$, G$^2$, G$^3$ and n are as defined above and
X$^1$ represents halogen or hydroxyl,
are reacted with a hydroxyalkylaniline derivative of the formula (XVI)

The oxathiincarboxylic acid derivatives of the formula (II) required as starting materials for carrying out the process (l) according to the invention have already been described further above, in connection with the process (a) according to the invention.

The formula (XVI) provides a general definition of the hydroxyalkylaniline derivatives furthermore required as starting materials for carrying out the process (l) according to the invention. In this formula (XVI), R$^1$, R$^2$, R$^3$, R$^4$, R$^5$ and X$^5$ preferably, particularly preferably and very particularly preferably have those meanings which have already been mentioned in connection with the description of the compounds of the formulae (I) and (VIII) according to the invention as being preferred, particularly preferred and very particularly preferred, respectively, for these radicals.

The hydroxyalkylaniline derivatives of the formula (XVI) are known and/or can be obtained by known methods (cf., for example, U.S. Pat. No. 3,917,592 or EP-A 0 824 099). If R$^5$ does not represent hydrogen, the radical R$^5$ can be introduced at the stage of the compounds of the formula (XVI) using customary derivatization methods. It is also possible to initially prepare compounds of the formula (VIII) in which $R^5$ represents hydrogen and then to derivatize the products obtained using customary methods [cf. the process (i) according to the invention].

Process (g)

Using, for example, N-(2-bromophenyl)-6-trifluoromethyl-2,3-dihydro-1,4-oxathiin-5-carboxamide and 1-hexyne as starting materials and a catalyst, the course of the process (g) according to the invention can be illustrated by the formula scheme below.

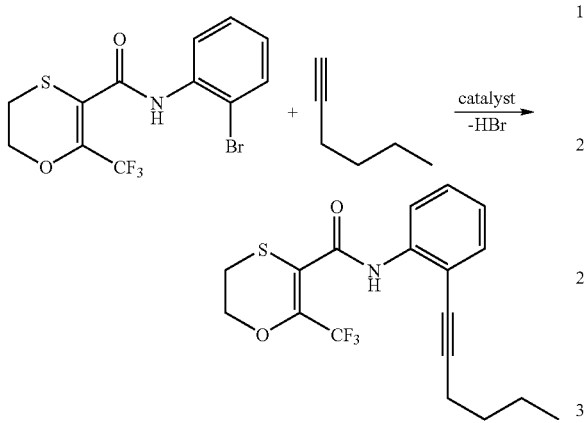

The halooxathiincarboxamides of the formula (IV) required as starting materials for carrying out the process (g) according to the invention have already been described further above, in connection with the process (c) according to the invention.

The formula (IX) provides a general definition of the alkynes furthermore required as starting materials for carrying out the process (g) according to the invention.

$A^5$ preferably represents $C_2$-$C_{10}$-alkyl which is optionally mono- to tetrasubstituted by identical or different substituents from the group consisting of fluorine, chlorine, bromine and $C_3$-$C_6$-cycloalkyl, where the cycloalkyl moiety for its part may optionally be substituted by halogen and/or $C_1$-$C_4$-alkyl.

$A^5$ particularly preferably represents in each case straight-chain or branched ethyl, propyl, butyl, pentyl, hexyl, heptyl or octyl, each of which may be attached in any position and each of which is optionally mono- to tetrasubstituted by identical or different substituents from the group consisting of fluorine, cyclopropyl, difluorocyclopropyl, cyclobutyl, cyclopentyl and cyclohexyl.

The alkynes of the formula (VI) are known chemicals for synthesis.

The formula (X) provides a general definition of the alkenes furthermore alternatively required as starting materials for carrying out the process (g) according to the invention.

$A^6$, $A^7$ and $A^8$ independently of one another preferably each represent hydrogen or alkyl which is optionally mono- to tetrasubstituted by identical or different substituents from the group consisting of fluorine, chlorine, bromine and $C_3$-$C_6$-cycloalkyl, where the cycloalkyl moiety for its part may optionally be substituted by halogen and/or $C_1$-$C_4$-alkyl and where the total number of carbon atoms of the open-chain part of the molecule does not exceed the number 12.

$A^6$, $A^7$ and $A^8$ independently of one another particularly preferably each represent hydrogen or in each case straight-chain or branched ethyl, propyl, butyl, pentyl, hexyl, heptyl or octyl, each of which may be attached in any position and each of which is optionally mono- to tetrasubstituted by identical or different substituents from the group consisting of fluorine, cyclopropyl, difluorocyclopropyl, cyclobutyl, cyclopentyl and cyclohexyl, where the total number of the carbon atoms of the open-chain part of the molecule does not exceed the number 12.

The alkenes of the formula (VII) are known chemicals for synthesis.

Process (h)

Using N-(2-acetylphenyl)[6-(trifluoromethyl)(2,3-dihydro-1,4-oxathiin-5-yl)]carboxamide and butyl(triphenyl)phosphonium iodide as starting materials, the course of the process (h) according to the invention can be illustrated by the formula scheme below:

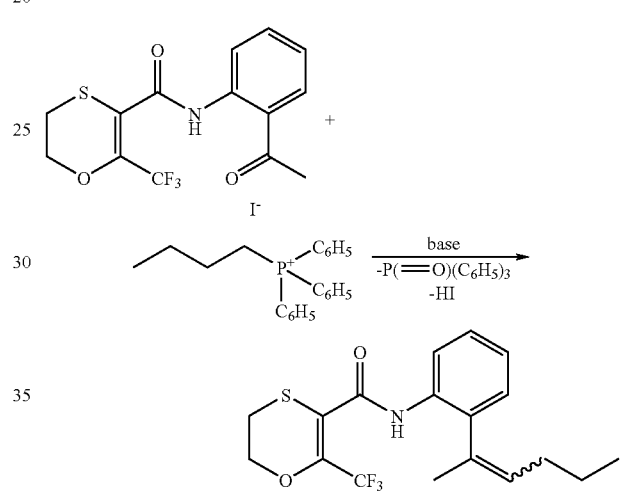

The formula (XI) provides a general definition of the ketones required as starting materials for carrying out the process (h) according to the invention. In this formula, $G^1$, $G^2$, $G^3$, n, $R^1$, $R^2$, $R^3$, $R^4$ and $R^5$ preferably, particularly preferably and very particularly preferably have those meanings which have already been mentioned in connection with the description of the compounds of the formula (I) according to the invention as being preferred, particularly preferred and very particularly preferred, respectively, for these radicals and this index.

$A^9$ preferably represents $C_2$-$C_{10}$-alkyl which is optionally mono- to tetrasubstituted by identical or different substituents from the group consisting of fluorine, chlorine, bromine and $C_3$-$C_6$-cycloalkyl, where the cycloalkyl moiety for its part may optionally be substituted by halogen and/or $C_1$-$C_4$-alkyl.

$A^9$ particularly preferably represents in each case straight-chain or branched ethyl, propyl, butyl, pentyl, hexyl, heptyl or octyl, each of which may be attached in any position and each of which is optionally mono- to tetrasubstituted by identical or different substituents from the group consisting of fluorine, cyclopropyl, difluoro-cyclopropyl, cyclobutyl, cyclopentyl and cyclohexyl.

The ketones of the formula (XI) have hitherto not been disclosed. As novel chemical compounds, they also form part of the subject-matter of the present application. They are obtained when m) oxathiincarboxylic acid derivatives of the formula (II)

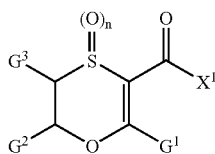
(II)

in which
G$^1$, G$^2$, G$^3$ and n are as defined above and
X$^1$ represents halogen or hydroxyl
are reacted with ketoanilines of the formula (XVII)

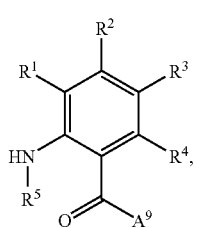
(XVII)

in which
R$^1$, R$^2$, R$^3$, R$^4$, R$^5$ and A$^9$ are as defined above,
if appropriate in the presence of a catalyst, if appropriate in the presence of a condensing agent, if appropriate in the presence of an acid binder and if appropriate in the presence of a diluent.

Process (m)

Using 6-trifluoromethyl-2,3-dihydro-1,4-oxathiin-5-carbonyl chloride and 1-(2-amino-phenyl)ethanone as starting materials, the course of the process (m) according to the invention can be illustrated by the formula scheme below:

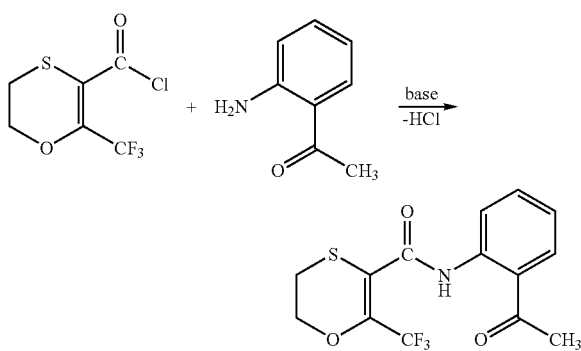

The oxathiincarboxylic acid derivatives of the formula (II) required as starting materials for carrying out the process (m) according to the invention have already been described further above, in connection with the process a) according to the invention.

The formula (XVII) provides a general definition of the ketoanilines furthermore required as starting materials for carrying out the process (m) according to the invention. In this formula (XVII), R$^1$, R$^2$, R$^3$, R$^4$, R$^5$ and A$^9$ preferably, particularly preferably and very particularly preferably have those meanings which have already been mentioned in connection with the description of the compounds of the formulae (I) and (XI) according to the invention as being preferred, particularly preferred and very particularly preferred, respectively, for these radicals.

The ketoanilines of the formula (XII) are generally customary chemicals for synthesis (cf., for example, J. Am. Chem. Soc. 1978, 100, 4852-4857 or U.S. Pat. No. 4,032, 573). If R$^5$ does not represent hydrogen, the radical R$^5$ can be introduced at the stage of the compounds of the formula (XVII) using customary derivatization methods. It is also possible to initially prepare compounds of the formula (XI) in which R$^5$ represents hydrogen and then to derivatize the products obtained using customary methods [cf. the process (i) according to the invention].

The formula (XII) provides a general definition of the phosphorus compounds furthermore required as starting materials for carrying out the process (h) according to the invention.

A$^{10}$ preferably represents C$_2$-C$_{10}$-alkyl which is optionally mono- to tetrasubstituted by identical or different substituents from the group consisting of chlorine, fluorine, bromine and C$_3$-C$_6$-cycloalkyl, where the cycloalkyl moiety for its part may optionally be substituted by halogen and/or C$_1$-C$_4$-alkyl.

A$^{10}$ particularly preferably represents in each case straight-chain or branched ethyl, propyl, butyl, pentyl, hexyl, heptyl or octyl, each of which may be attached in any position and each of which is optionally mono- to tetrasubstituted by identical or different substituents from the group consisting of fluorine, cyclopropyl, difluoro-cyclopropyl, cyclobutyl, cyclopentyl and cyclohexyl.

Px preferably represents a grouping —P$^+$(C$_6$H$_5$)$_3$Cl$^-$, —P$^+$(C$_6$H$_5$)$_3$Br$^-$, —P$^+$(C$_6$H$_5$)$_3$I$^-$, —P(=O)(OCH$_3$)$_3$ or —P(=O)(OC$_2$H$_5$)$_3$.

The phosphorus compounds of the formula (XII) are known and/or can be prepared by known processes (cf., for example, Justus Liebigs Ann. Chem. 1953, 580, 44-57 or Pure Appl. Chem. 1964, 9, 307-335).

Process (i)

Using N-[2-(1,3-dimethylbutyl)phenyl]-2-(trifluoromethyl)-5,6-dihydro-1,4-oxathiin-3-carboxamide and acetyl chloride as starting materials, the course of the process (i) according to the invention can be illustrated by the formula scheme below:

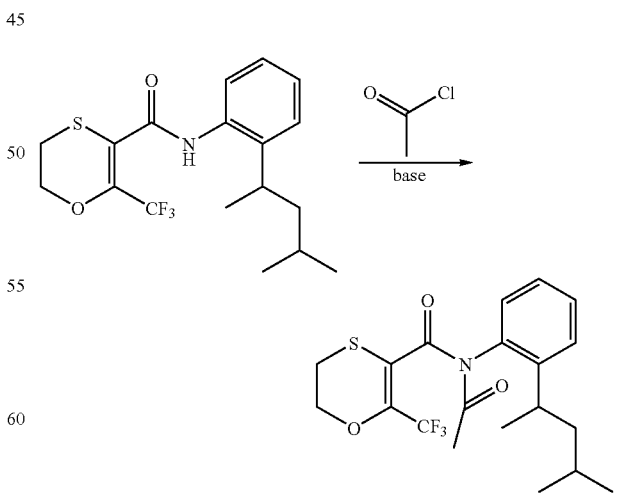

The formula (Ib) provides a general definition of the iodopyrazolylcarboxanilides required as starting materials for carrying out the process (i) according to the invention. In this formula (Ib), $G^1$, $G^2$, $G^3$, n, $R^1$, $R^2$, $R^3$, $R^4$ and Z preferably, particularly preferably and very particularly preferably have those meanings which have already been mentioned in connection with the description of the compounds of the formula (I) according to the invention as being preferred, particularly preferred and very particularly preferred, respectively, for these radicals and this index.

The compounds of the formula (Ib) are compounds according to the invention and can be prepared according to processes (a) to (h).

The formula (XIII) provides a general definition of the halides furthermore required as starting materials for carrying out the process (i) according to the invention. In this formula (XIII), $R^{5-1}$ preferably, particularly preferably and very particularly preferably has those meanings which have already been mentioned above in connection with the description of the compounds of the formula (Ig) as being preferred, particularly preferred and very particularly preferred for these radicals. $X^6$ represents chlorine, bromine or iodine.

Halides of the formula (XIII) are known.

Reaction Conditions

Suitable diluents for carrying out the processes (a), (j), (k), (l) and (m) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethylformamide, N,N-dimethyl-acetamide, N-methylformanilide, N-methylpyrrolidone or hexamethylphosphoric triamide; mixtures thereof with water or pure water.

The processes (a), (j), (k), (l) and (m) according to the invention are, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, lithium diisopropylamide, sodium methoxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethylbenzylamine, pyridine, N-methyl-piperidine, N-methylmorpholine, N,N-dimethylaminopyridine, diazabicyclooctane (DABCO), diazabicyclononene (DBN) or diazabicycloundecene (DBU).

The processes (a), (j), (k), (l) and (m) according to the invention are, if appropriate, carried out in the presence of a suitable condensing agent. Suitable condensing agents are all condensing agents which are customarily used for such amidation reactions. Examples which may be mentioned are acid halide formers, such as phosgene, phosphorus tribromide, phosphorus trichloride, phosphorus pentachloride, phosphorus oxychloride or thionyl chloride; anhydride formers, such as ethyl chloroformate, methyl chloroformate, isopropyl chloroformate, isobutyl chloroformate or methanesulfonyl chloride; carbodiimides, such as N,N'-dicyclohexylcarbodiimide (DCC), or other customary condensing agents, such as phosphorus pentoxide, polyphosphoric acid, N,N'-carbonyldiimidazole, 2-ethoxy-N-ethoxycarbonyl-1,2-dihydroquinoline (EEDQ), triphenylphosphine/carbon tetrachloride or bromotripyrrolidinophosphonium hexafluorophosphate.

The processes (a), (j), (k), (l) and (m) according to the invention are, if appropriate, carried out in the presence of a catalyst. Examples which may be mentioned are 4-dimethylaminopyridine, 1-hydroxybenzotriazole and dimethylformamide.

When carrying out the processes (a), (j), (k), (l) and (m) according to the invention, the reaction temperatures can be varied within a relatively wide range. In general, the processes are carried out at temperatures of from 0° C. to 150° C., preferably at temperatures of from 0° C. to 80° C.

For carrying out the process (a) according to the invention for preparing the compounds of the formula (I), in general from 0.8 to 15 mol, preferably from 0.8 to 8 mol, of aniline derivative of the formula (III) are employed per mole of the oxathiincarboxylic acid derivative of the formula (II).

For carrying out the process (j) according to the invention for preparing the compounds of the formula (IV), in general from 0.8 to 15 mol, preferably from 0.8 to 8 mol, of haloaniline of the formula (XIV) are employed per mole of the oxathiincarboxylic acid derivative of the formula (II).

For carrying out the process (k) according to the invention for preparing the compounds of the formula (VI), in general from 0.8 to 15 mol, preferably from 0.8 to 8 mol, of aniline-boronic acid derivative of the formula (XV) are employed per mole of the oxathiincarboxylic acid derivative of the formula (II).

For carrying out the process (l) according to the invention for preparing the compounds of the formula (VIII), in general from 0.8 to 15 mol, preferably from 0.8 to 8 mol, of hydroxyalkylaniline derivative of the formula (XVI) are employed per mole of the oxathiincarboxylic acid derivative of the formula (II).

For carrying out the process (m) according to the invention for preparing the compounds of the formula (IX), in general from 0.8 to 15 mol, preferably from 0.8 to 8 mol, of ketoaniline of the formula (XVII) are employed per mole of the oxathiincarboxylic acid derivative of the formula (II).

Suitable diluents for carrying out the processes (b), (c) and (d) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethyl-acetamide, N-methylformanilide, N-methylpyrrolidone or hexamethylphosphoric triamide; esters, such as methyl acetate or ethyl acetate; sulfoxides, such as dimethyl sulfoxide; sulfones, such as sulfolane; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether, mixtures thereof with water or pure water.

When carrying out the processes (b), (c) and (d) according to the invention, the reaction temperatures can be varied within a relatively wide range. In general, the processes are carried out at temperatures of from 0° C. to 180° C., preferably at temperatures of from 20° C. to 150° C.

The processes (b), (c) and (d) according to the invention are, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, fluorides, phosphates, carbonates or bicarbonates, such as, for example, sodium hydride, sodium amide, lithium diisopropylamide, sodium methoxide, sodium ethoxide, potassium tert-butoxide, sodium hydroxide, potassium hydroxide, sodium acetate, sodium phosphate, potassium phosphate, potassium fluoride, cesium fluoride, sodium carbonate, potassium carbonate, potassium bicarbonate, sodium bicarbonate or cesium carbonate, and also tertiary amines, such as trimethylamine, triethylamine, tributylamine, N,N-dimethylaniline, N,N-dimethylbenzylamine, pyridine, N-methylpiperidine, N-methyl-morpholine, N,N-dimethylaminopyridine, diazabicyclooctane (DABCO), diazabicyclononene (DBN) or diazabicycloundecene (DBU).

The processes (b), (c) and (d) according to the invention are carried out in the presence of a catalyst, such as, for example, a palladium salt or complex. Suitable catalysts are, preferably, palladium chloride, palladium acetate, tetrakis(triphenylphosphine)palladium, bis-triphenyl-phosphine)palladiumdichloride or 1,1'-bis(diphenylphosphino) ferrocenepalladium(II) chloride.

It is also possible to generate a palladium complex in the reaction mixture by separately adding a palladium salt and a complex ligand, such as, for example, triethylphosphine, tri-tert-butylphosphine, tricyclohexylphosphine, 2-(dicyclohexylphosphine)biphenyl, 2-(di-tert-butylphosphine)biphenyl, 2-(dicyclohexylphosphine)-2'-(N,N-dimethylamino) biphenyl, triphenylphosphine, tris-(o-tolyl)phosphine, sodium 3-(diphenylphosphino)benzenesulfonate, tris-2-(methoxyphenyl)phosphine, 2,2'-bis(diphenylphosphine)-1, 1'-binaphthyl, 1,4-bis(di-phenylphosphine)butane, 1,2-bis(diphenylphosphine)ethane, 1,4-bis(dicyclohexylphosphine)-butane, 1,2-bis(dicyclohexylphosphine)ethane, 2-(dicyclohexylphosphine)-2'-(N,N-dimethylamino)biphenyl, bis(diphenylphosphino) ferrocene or tris-(2,4-tert-butylphenyl)-phosphite to the reaction.

To carry out the process (b) according to the invention for preparing the compounds of the formula (I), in general from 1 to 15 mol, preferably from 2 to 8 mol, of the boronic acid derivative of the formula (V) are employed per mole of the halooxathiincarboxamide of the formula (IV).

To carry out the process (c) according to the invention for preparing the compounds of the formula (I), in general from 0.8 to 15 mol, preferably from 0.8 to 8 mol, of the phenyl derivative of the formula (VII) are employed per mole of the oxathiincarboxamideboronic acid derivative of the formula (VI).

To carry out the process (d) according to the invention for preparing the compounds of the formula (I), in general from 0.8 to 15 mol, preferably from 0.8 to 8 mol, of the phenyl derivative of the formula (VII) and from 0.8 to 15 mol, preferably from 0.8 to 8 mol, of 4,4,4',4',5,5,5',5'-octamethyl-2, 2'-bis-1,3,2-dioxaborolane are employed per mole of the halooxathiincarboxamide of the formula (IV).

Suitable diluents for carrying out the process (e) according to the invention are all inert organic solvents. These preferably include aliphatic or alicyclic hydrocarbons, such as, for example, petroleum ether, hexane, heptane, cyclohexane, methylcyclohexane or decalin; ethers, such as diethyl ether, diisopropyl ether, methyl t-butyl ether, methyl t-amyl ether, dioxane, tetrahydrofuran, 1,2-dimethoxyethane or 1,2-diethoxyethane; alcohols, such as methanol, ethanol, n- or i-propanol, n-, i-, sec- or tert-butanol, ethanediol, propane-1, 2-diol, ethoxyethanol, methoxyethanol, diethylene glycol monomethyl ether, diethylene glycol monoethyl ether, mixtures thereof with water or pure water.

The (e) process according to the invention is carried out in the presence of a catalyst. Suitable catalysts are all those commonly employed for hydrogenations. Examples which may be mentioned are: Raney nickel, palladium and platinum, if appropriate on a support, such as, for example, activated carbon.

When carrying out the process (e) according to the invention, the reaction temperatures can be varied within a relatively wide range. In general, the reaction is carried out at temperatures of from 0° C. to 150° C., preferably at temperatures of from 20° C. to 100° C.

Suitable diluents for carrying out the process (f) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or i-butyronitrile or benzonitrile; amides, such as N,N-dimethyl-formamide, N,N-dimethylacetamide, N-methylformanilide, N-methylpyrrolidone or hexamethylphosphoric triamide; esters, such as methyl acetate or ethyl acetate; sulfoxides, such as dimethyl sulfoxide; sulfones, such as sulfolane; alcohols, such as methanol, ethanol, n- or i-propanol, n-, i-, sec- or tert-butanol, ethanediol, propane-1,2-diol, ethoxyethanol, methoxy-ethanol, diethylene glycol monomethyl ether, diethylene glycol monoethyl ether, mixtures thereof with water or pure water.

The process (f) according to the invention is, if appropriate, carried out in the presence of an acid. Suitable acids are all inorganic and organic protic and Lewis acids, and also all polymeric acids. These include, for example, hydrogen chloride, sulfuric acid, phosphoric acid, formic acid, acetic acid, trifluoroacetic acid, methanesulfonic acid, trifluoromethanesulfonic acid, toluenesulfonic acid, boron trifluoride (also as etherate), boron tribromide, aluminum trichloride, titanium tetrachloride, tetrabutyl orthotitanate, zinc chloride, iron(III) chloride, antimony pentachloride, acidic ion exchangers, acidic aluminas and acidic silica gels.

When carrying out the process (f) according to the invention, the reaction temperatures can be varied within a relatively wide range. In general, the process is carried out at temperatures of from 0° C. to 150° C., preferably at temperatures of from 0° C. to 100° C.

Suitable diluents for carrying out the process (g) according to the invention are all inert organic solvents. These preferably include nitriles, such as acetonitrile, propionitrile, n- or i-butyronitrile or benzonitrile, or amides, such as N,N-dimethylformamide, N,N-dimethyl-acetamide, N-methylformanilide, N-methylpyrrolidone or hexamethylphosphoric triamide.

The process (g) according to the invention is, if appropriate, carried out in the presence of a suitable acid acceptor. Suitable acid acceptors are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethylbenzyl-amine, pyridine, N-methylpiperidine, N-methylmorpholine, N,N-dimethylaminopyridine, diazabicyclooctane (DABCO), diazabicyclononene (DBN) or diazabicycloundecene (DBU).

The process (g) according to the invention is carried out in the presence of one or more catalysts.

Suitable catalysts are in particular palladium salts or complexes. These are preferably palladium chloride, palladium acetate, tetrakis(triphenylphosphine)palladium or bis-(triphenylphosphine)palladium dichloride. It is also possible to generate a palladium complex in the reaction mixture by adding a palladium salt and a complex ligand separately to the reaction.

Preferred ligands are organophosphorus compounds. Examples which may be mentioned are: triphenylphosphine, tri-o-tolylphosphine, 2,2'-bis(diphenylphosphino)-1,1'-binaphthyl, dicyclohexylphosphinebiphenyl, 1,4-bis(diphenylphosphino)butane, bisdiphenylphosphino-ferrocene, di-(tert-butylphosphino)biphenyl, di(cyclohexylphosphino)biphenyl, 2-dicyclohexylphosphino-2'-N,N-dimethylaminobiphenyl, tricyclohexylphosphine, tri-tert-butylphosphine. However, ligands may also be dispensed with.

Furthermore, the process (g) according to the invention is, if appropriate, carried out in the presence of a further metal salt, such as a copper salt, for example copper(I) iodide.

When carrying out the process (g) according to the invention, the reaction temperatures can be varied within a relatively wide range. In general, the process is carried out at temperatures of from 20° C. to 180° C., preferably at temperatures of from 50° C. to 150° C.

For carrying out the process (g) according to the invention for preparing the compounds of the formula (I), in general from 1 to 5 mol, preferably from 1 to 2 mol, of the alkyne of the formula (IX) or the alkene of the formula (X) are employed per mole of the halooxathiincarboxamide of the formula (IV).

Suitable diluents for carrying out the process (h) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl t-butyl ether, methyl t-amyl ether, dioxane, tetrahydrofuran, 1,2-dimethoxyethane, 1,2-diethoxyethane or anisole; nitriles, such as acetonitrile, propionitrile, n- or i-butyronitrile or benzonitrile; amides, such as N,N-dimethylformamide, N,N-dimethylacetamide, N-methyl-formanilide, N-methylpyrrolidone or hexamethylphosphoric triamide; esters, such as methyl acetate or ethyl acetate; sulfoxides, such as dimethylsulfoxide; sulfones, such as sulfolane; alcohols, such as methanol, ethanol, n- or i-propanol, n-, i-, sec- or tert-butanol, ethanediol, propane-1,2-diol, ethoxyethanol, methoxyethanol, diethylene glycol monomethyl ether, diethylene glycol monoethyl ether.

The process (h) according to the invention is, if appropriate, carried out in the presence of a suitable acid acceptor.

Suitable acid acceptors are all customary strong bases. These preferably include alkaline earth metal or alkali metal hydrides, hydroxides, amides, alkoxides or alkali metal hydrocarbon compounds, such as, for example, sodium hydride, sodium hydroxide, potassium hydroxide, sodium amide, lithium diisopropylamide, sodium methoxide, sodium ethoxide, potassium tert-butoxide, methyllithium, phenyllithium or butyllithium.

When carrying out the process (h) according to the invention, the reaction temperatures can be varied within a relatively wide range. In general, the process is carried out at temperatures of from −80° C. to 150° C., preferably at temperatures of from −30° C. to 80° C.

To carry out the process (h) according to the invention for preparing compounds of the formula (I), in general from 1 to 5 mol, preferably from 1 to 2 mol, of the phosphorus compound of the formula (XII) are employed per mole of the ketone of the formula (XI).

Suitable diluents for carrying out the process (i) according to the invention are all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; or amides, such as N,N-dimethylformamide, N,N-dimethylacetamide, N-methylformanilide, N-methylpyrrolidone or hexamethylphosphoric triamide.

The process (i) according to the invention is carried out in the presence of a base. Suitable bases are all customary inorganic or organic bases. These preferably include alkaline earth metal or alkali metal hydrides, hydroxides, amides, alkoxides, acetates, carbonates or bicarbonates, such as, for example, sodium hydride, sodium amide, sodium methoxide, sodium ethoxide, potassium tert-butoxide, sodium hydroxide, potassium hydroxide, ammonium hydroxide, sodium acetate, potassium acetate, calcium acetate, ammonium acetate, sodium carbonate, potassium carbonate, potassium bicarbonate, sodium bicarbonate or cesium carbonate, and also tertiary amines, such as trimethylamine, triethylamine, tributylamine, N,N-dimethylaniline, N,N-dimethylbenzylamine, pyridine, N-methyl-piperidine, N-methylmorpholine, N,N-dimethylaminopyridine, diazabicyclooctane (DABCO), diazabicyclononene (DBN) or diazabicycloundecene (DBU).

When carrying out the process (i) according to the invention, the reaction temperatures can be varied within a relatively wide range. In general, the process is carried out at temperatures of from 0° C. to 150° C., preferably at temperatures of from 20° C. to 110° C.

To carry out the process (i) according to the invention for preparing the compounds of the formula (I), in general from 0.2 to 5 mol, preferably from 0.5 to 2 mol, of the halide of the formula (XIII) are employed per mole of the oxathiincarboxamide of the formula (Ib).

All processes according to the invention are generally carried out under atmospheric pressure. However, it is also possible to operate under elevated or reduced pressure—in general between 0.1 bar and 10 bar.

The compounds according to the invention have potent microbicidal activity and can be employed for controlling undesirable microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

Some pathogens causing fungal and bacterial diseases which come under the generic names listed above may be mentioned as examples, but not by way of limitation:

Xanthomonas species, such as, for example, Xanthomonas campestris pv. oryzae;
Pseudomonas species, such as, for example, Pseudomonas syringae pv. lachrymans;
Erwinia species, such as, for example, Erwinia amylovora;
Pythium species, such as, for example, Pythium ultimum;
Phytophthora species, such as, for example, Phytophthora infestans;
Pseudoperonospora species, such as, for example, Pseudoperonospora humuli or Pseudoperonospora cubensis;
Plasmopara species, such as, for example, Plasmopara viticola;
Bremia species, such as, for example, Bremia lactucae;
Peronospora species, such as, for example, Peronospora pisi or P. brassicae;
Erysiphe species, such as, for example, Erysiphe graminis;
Sphaerotheca species, such as, for example, Sphaerotheca fuliginea;
Podosphaera species, such as, for example, Podosphaera leucotricha;
Venturia species, such as, for example, Venturia inaequalis;
Pyrenophora species, such as, for example, Pyrenophora teres or P. graminea (conidia form: Drechslera, syn: Helminthosporium);
Cochliobolus species, such as, for example, Cochliobolus sativus (conidia form: Drechslera, syn: Helminthosporium);
Uromyces species, such as, for example, Uromyces appendiculatus;
Puccinia species, such as, for example, Puccinia recondita;
Sclerotinia species, such as, for example, Sclerotinia sclerotiorum;
Tilletia species, such as, for example, Tilletia caries;
Ustilago species, such as, for example, Ustilago nuda or Ustilago avenae;
Pellicularia species, such as, for example, Pellicularia sasakii;
Pyricularia species, such as, for example, Pyricularia oryzae;
Fusarium species, such as, for example, Fusarium culmorum;
Botrytis species, such as, for example, Botrytis cinerea;
Septoria species, such as, for example, Septoria nodorum;
Leptosphaeria species, such as, for example, Leptosphaeria nodorum;
Cercospora species, such as, for example, Cercospora canescens;
Alternaria species, such as, for example, Alternaria brassicae; and
Pseudocercosporella species, such as, for example, Pseudocercosporella herpotrichoides.

The active compounds according to the invention also have very good fortifying action in plants. Accordingly, they can be used for mobilizing the defenses of the plant against attack by undesirable microorganisms.

In the present context, plant-fortifying (resistance-inducing) substances are to be understood as meaning those substances which are capable of stimulating the defense system of plants such that, when the treated plants are subsequently inoculated with undesirable microorganisms, they show substantial resistance to these microorganisms.

In the present case, undesirable microorganisms are to be understood as meaning phytopathogenic fungi, bacteria and viruses. Accordingly, the substances according to the invention can be used to protect plants for a certain period after the treatment against attack by the pathogens mentioned. The period for which protection is provided generally extends over 1 to 10 days, preferably 1 to 7 days, after the treatment of the plants with the active compounds.

The fact that the active compounds are well tolerated by plants at the concentrations required for controlling plant diseases permits the treatment of above-ground parts of plants, of propagation stock and seeds, and of the soil.

The active compounds according to the invention can be used with particularly good results for controlling cereal diseases, such as, for example, against Pyrenophora species, diseases in viticulture and in the cultivation of fruit and vegetables, such as, for example, against Botrytis, Venturia or Alternaria species.

The active compounds according to the invention are also suitable for increasing the yield of crops. In addition, they show reduced toxicity and are well tolerated by plants.

At certain concentrations and application rates, the active compounds according to the invention can also if appropriate be used as herbicides, for influencing plant growth and for controlling animal pests. If appropriate, they can also be used as intermediates and precursors for the synthesis of further active compounds.

All plants and plant parts can be treated in accordance with the invention. Plants are to be understood as meaning in the present context all plants and plant populations such as desired and undesired wild plants or crop plants (including naturally occurring crop plants). Crop plants can be plants which can be obtained by conventional plant breeding and optimization methods or by biotechnological and recombinant methods or by combinations of these methods, including the transgenic plants and inclusive of the plant cultivars protectable or not protectable by plant breeders' rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. The plant parts also include harvested material, and vegetative and generative propagation material, for example cuttings, tubers, rhizomes, offshoots and seeds.

Treatment according to the invention of the plants and plant parts with the active compounds is carried out directly or by allowing the compounds to act on the surroundings, environment or storage space by the customary treatment methods, for example by immersion, spraying, evaporation, fogging, scattering, painting on, and, in the case of propagation material, in particular in the case of seeds, also by applying one or more coats.

In the protection of materials, the substances according to the invention can be employed for protecting industrial materials against infection with, and destruction by, undesired microorganisms.

Industrial materials in the present context are understood as meaning nonliving materials which have been prepared for use in industry. For example, industrial materials which are intended to be protected by active compounds according to the invention from microbial change or destruction can be adhesives, sizes, paper and board, textiles, leather, wood, paints and plastic articles, cooling lubricants and other materials which can be infected with, or destroyed by, microorganisms. Parts of production plants, for example cooling-water circuits, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood.

Microorganisms capable of degrading or changing the industrial materials which may be mentioned are, for example, bacteria, fungi, yeasts, algae and slime organisms. The active compounds according to the invention preferably act against fungi, in particular molds, wood-discoloring and wood-destroying fungi (Basidiomycetes), and against slime organisms and algae.

Microorganisms of the following genera may be mentioned as examples:
*Alternaria*, such as *Alternaria tenuis*,
*Aspergillus*, such as *Aspergillus niger*,
*Chaetomium*, such as *Chaetomium globosum*,
*Coniophora*, such as *Coniophora puetana*,
*Lentinus*, such as *Lentinus tigrinus*,
*Penicillium*, such as *Penicillium glaucum*,
*Polyporus*, such as *Polyporus versicolor*,
*Aureobasidium*, such as *Aureobasidium pullulans*,
*Sclerophoma*, such as *Sclerophoma pityophila*,
*Trichoderma*, such as *Trichoderma viride*,
*Escherichia*, such as *Escherichia coli*,
*Pseudomonas*, such as *Pseudomonas aeruginosa*, and
*Staphylococcus*, such as *Staphylococcus aureus*.

Depending on their particular physical and/or chemical properties, the active compounds can be converted to the customary formulations, such as solutions, emulsions, suspensions, powders, foams, pastes, granules, aerosols and microencapsulations in polymeric substances and in coating compositions for seeds, and ULV cool and warm fogging formulations.

These formulations are produced in a known manner, for example by mixing the active compounds with extenders, that is, liquid solvents, liquefied gases under pressure, and/or solid carriers, optionally with the use of surfactants, that is emulsifiers and/or dispersants, and/or foam formers. If the extender used is water, it is also possible to employ, for example, organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide or dimethyl sulfoxide, or else water. Liquefied gaseous extenders or carriers are to be understood as meaning liquids which are gaseous at standard temperature and under atmospheric pressure, for example aerosol propellants such as halogenated hydrocarbons, or else butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, corn cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates, or else protein hydrolyzates. Suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 percent by weight of active compound, preferably between 0.5 and 90%.

The active compounds according to the invention can be used as such or in their formulations, also in a mixture with known fungicides, bactericides, acaricides, nematicides or insecticides, to broaden, for example, the activity spectrum or to prevent development of resistance. In many cases, synergistic effects are obtained, i.e. the activity of the mixture is greater than the activity of the individual components.

Examples of suitable mixing components are the following compounds:

Fungicides:
2-phenylphenol; 8-hydroxyquinoline sulfate; acibenzolar-5-methyl; aldimorph; amidoflumet; ampropylfos; ampropylfos-potassium; andoprim; anilazine; azaconazole; azoxystrobin; benalaxyl; benodanil; benomyl; benthiavalicarb-isopropyl; benzamacril; benzamacril-isobutyl; bilanafos; binapacryl; biphenyl; bitertanol; blasticidin-S; bromuconazole; bupirimate; buthiobate; butylamine; calcium polysulfide; capsimycin; captafol; captan; carbendazim; carboxin; carpropamid; carvone; chinomethionat; chlobenthiazone; chlorfenazole; chloroneb; chlorothalonil; chlozolinate; clozylacon; cyazofamid; cyflufenamid; cymoxanil; cyproconazole; cyprodinil; cyprofuram; Dagger G; debacarb; dichlofluanid; dichlone; dichlorophen; diclocymet; diclomezine; dicloran; diethofencarb; difenoconazole; diflumetorim; dimethirimol; dimethomorph; dimoxystrobin; diniconazole; diniconazole-M; dinocap; diphenylamine; dipyrithione; ditalimfos; dithianon; dodine; drazoxolon; edifenphos; epoxiconazole; ethaboxam; ethirimol; etridiazole; famoxadone; fenamidone; fenapanil; fenarimol; fenbuconazole; fenfuram; fenhexamid; fenitropan; fenoxanil; fenpiclonil; fenpropidin; fenpropimorph; ferbam; fluazinam; flubenzimine; fludioxonil; flumetover; flumorph; fluoromide; fluoxastrobin; fluquinconazole; flurprimidol; flusilazole; flusulfamide; flutolanil; flutriafol; folpet; fosetyl-Al; fosetyl-sodium; fuberidazole; furalaxyl; furametpyr; furcarbanil; furmecyclox; guazatine; hexachlorobenzene; hexaconazole; hymexazole; imazalil; imibenconazole; iminoctadine triacetate; iminoctadine tris(albesil); iodocarb; ipconazole; iprobenfos; iprodione; iprovalicarb; irumamycin; isoprothiolane; isovaledione; kasugamycin; kresoxim-methyl; mancozeb; maneb; meferimzone; mepanipyrim; mepronil;

metalaxyl; metalaxyl-M; metconazole; methasulfocarb; methfuroxam; metiram; metominostrobin; metsulfovax; mildiomycin; myclobutanil; myclozolin; natamycin; nicobifen; nitrothal-isopropyl; noviflumuron; nuarimol; ofurace; orysastrobin; oxadixyl; oxolinic acid; oxpoconazole; oxycarboxin; oxyfenthiin; paclobutrazole; pefurazoate; penconazole; pencycuron; phosdiphen; phthalide; picoxystrobin; piperalin; polyoxins; polyoxorim; probenazole; prochloraz; procymidone; propamocarb; propanosine-sodium; propiconazole; propineb; proquinazid; prothioconazole; pyraclostrobin; pyrazophos; pyrifenox; pyrimethanil; pyroquilon; pyroxyfur; pyrrolenitrine; quinconazole; quinoxyfen; quintozene; simeconazole; spiroxamine; sulfur; tebuconazole; tecloftalam; tecnazene; tetcyclacis; tetraconazole; thiabendazole; thicyofen; thifluzamide; thiophanate-methyl; thiram; tioxymid; tolclofos-methyl; tolylfluanid; triadimefon; triadimenol; triazbutil; triazoxide; tricyclamide; tricyclazole; tridemorph; trifloxystrobin; triflumizole; triforine; triticonazole; uniconazole; validamycin A; vinclozolin; zineb; ziram; zoxamide; (2S)-N-[2-[4-[[3-(4-chlorophenyl)-2-propynyl]oxy]-3-methoxyphenyl]ethyl]-3-methyl-2-[(methylsulfonyl)amino]butanamide; 1-(1-naphthalenyl)-1H-pyrrole-2,5-dione; 2,3,5,6-tetrachloro-4-(methylsulfonyl)pyridine; 2-amino-4-methyl-N-phenyl-5-thiazolecarboxamide; 2-chloro-N-(2,3-dihydro-1,1,3-trimethyl-1H-inden-4-yl)-3-pyridinecarboxamide; 3,4,5-trichloro-2,6-pyridinedicarbonitrile; actinovate; cis-1-(4-chlorophenyl)-2-(1H-1,2,4-triazol-1-yl)cycloheptanol; methyl 1-(2,3-dihydro-2,2-dimethyl-1H-inden-1-yl)-1H-imidazole-5-carboxylate; monopotassium carbonate; N-(6-methoxy-3-pyridinyl)cyclopropanecarboxamide; N-butyl-8-(1,1-dimethylethyl)-1-oxaspiro[4.5]decane-3-amine; sodium tetrathiocarbonate; and copper salts and preparations, such as Bordeaux mixture; copper hydroxide; copper naphthenate; copper oxychloride; copper sulfate; cufraneb; cuprous oxide; mancopper; oxinecopper.

Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulfate and other copper preparations.

Insecticides/Acaricides/Nematicides:
abamectin, ABG-9008, acephate, acequinocyl, acetamiprid, acetoprole, acrinathrin, AKD-1022, AKD-3059, AKD-3088, alanycarb, aldicarb; aldoxycarb, allethrin, allethrin 1R-isomers, alpha-cypermethrin (alphamethrin), amidoflumet, aminocarb, amitraz, avermectin, AZ-60541, azadirachtin, azamethiphos, azinphos-methyl, azinphos-ethyl, azocyclotin, *Bacillus popilliae, Bacillus sphaericus, Bacillus subtilis, Bacillus thuringiensis, Bacillus thuringiensis* strain EG-2348, *Bacillus thuringiensis* strain GC-91, *Bacillus thuringiensis* strain NCTC-11821, baculoviruses, *Beauveria bassiana, Beauveria tenella*, bendiocarb, benfuracarb, bensultap, benzoximate, beta-cyfluthrin, beta-cypermethrin, bifenazate, bifenthrin, binapacryl, bioallethrin, bioallethrin-5-cyclopentyl-isomer, bioethanomethrin, biopermethrin, bioresmethrin, bistrifluron, BPMC, brofenprox, bromophos-ethyl, bromopropylate, bromfenvinfos (-methyl), BTG-504, BTG-505, bufencarb, buprofezin, butathiofos, butocarboxim, butoxycarboxim, butylpyridaben, cadusafos, camphechlor, carbaryl, carbofuran, carbophenothion, carbosulfan, cartap, CGA-50439, chinomethionat, chlordane, chlordimeform, chloethocarb, chlorethoxyfos, chlorfenapyr, chlorfenvinphos, chlorfluazuron, chlormephos, chlorobenzilate, chloropicrin, chlorproxyfen, chlorpyrifos-methyl, chlorpyrifos (-ethyl), chlovaporthrin, chromafenozide, cis-cypermethrin, cis-resmethrin, cis-permethrin, clocythrin, cloethocarb, clofentezine, clothianidin, clothiazoben, codlemone, coumaphos, cyanofenphos, cyanophos, cycloprene, cycloprothrin, *Cydia pomonella*, cyfluthrin, cyhalothrin, cyhexatin, cypermethrin, cyphenothrin (1R-trans-isomer), cyromazine, DDT, deltamethrin, demeton-5-methyl, demeton-5-methylsulfone, diafenthiuron, dialifos, diazinon, dichlofenthion, dichlorvos, dicofol, dicrotophos, dicyclanil, diflubenzuron, dimethoate, dimethylvinphos, dinobuton, dinocap, dinotefuran, diofenolan, disulfoton, docusat-sodium, dofenapyn, DOWCO-439, eflusilanate, emamectin, emamectin-benzoate, empenthrin (1R-isomer), endosulfan, *Entomopthora* spp., EPN, esfenvalerate, ethiofencarb, ethiprole, ethion, ethoprophos, etofenprox, etoxazole, etrimfos, famphur, fenamiphos, fenazaquin, fenbutatin oxide, fenfluthrin, fenitrothion, fenobucarb, fenothiocarb, fenoxacrim, fenoxycarb, fenpropathrin, fenpyrad, fenpyrithrin, fenpyroximate, fensulfothion, fenthion, fentrifanil, fenvalerate, fipronil, flonicamid, fluacrypyrim, fluazuron, flubenzimine, flubrocythrinate, flucycloxuron, flucythrinate, flufenerim, flufenoxuron, flufenprox, flumethrin, flupyrazofos, flutenzin (flufenzine), fluvalinate, fonofos, formetanate, formothion, fosmethilan, fosthiazate, fubfenprox (fluproxyfen), furathiocarb, gamma-HCH, gossyplure, grandlure, granulosis viruses, halfenprox, halofenozide, HCH, HCN-801, heptenophos, hexaflumuron, hexythiazox, hydramethylnone, hydroprene, IKA-2002, imidacloprid, imiprothrin, indoxacarb, iodofenphos, iprobenfos, isazofos, isofenphos, isoprocarb, isoxathion, ivermectin, japonilure, kadethrin, nuclear polyhedrosis viruses, kinoprene, lambda-cyhalothrin, lindane, lufenuron, malathion, mecarbam, mesulfenfos, metaldehyde, metam-sodium, methacrifos, methamidophos, *Metarhizium anisopliae, Metarhizium flavoviride*, methidathion, methiocarb, methomyl, methoprene, methoxychlor, methoxyfenozide, metolcarb, metoxadiazone, mevinphos, milbemectin, milbemycin, MKI-245, MON-45700, monocrotophos, moxidectin, MTI-800, naled, NC-104, NC-170, NC-184, NC-194, NC-196, niclosamide, nicotine, nitenpyram, nithiazine, NNI-0001, NNI-0101, NNI-0250, NNI-9768, novaluron, noviflumuron, OK-5101, OK-5201, OK-9601, OK-9602, OK-9701, OK-9802, omethoate, oxamyl, oxydemeton-methyl, *Paecilomyces fumosoroseus*, parathion-methyl, parathion (-ethyl), permethrin (cis-, trans-), petroleum, PH-6045, phenothrin (1R-trans isomer), phenthoate, phorate, phosalone, phosmet, phosphamidon, phosphocarb, phoxim, piperonyl butoxide, pirimicarb, pirimiphosmethyl, pirimiphosethyl, prallethrin, profenofos, promecarb, propaphos, propargite, propetamphos, propoxur, prothiofos, prothoate, protrifenbute, pymetrozine, pyraclofos, pyresmethrin, pyrethrum, pyridaben, pyridalyl, pyridaphenthion, pyridathion, pyrimidifen, pyriproxyfen, quinalphos, resmethrin, RH-5849, ribavirin, RU-12457, RU-15525, S-421, S-1833, salithion, sebufos, SI-0009, silafluofen, spinosad, spirodiclofen, spiromesifen, sulfluramid, sulfotep, sulprofos, SZI-121, tau-fluvalinate, tebufenozide, tebufenpyrad, tebupirimfos, teflubenzuron, tefluthrin, temephos, temivinphos, terbam, terbufos, tetrachlorvinphos, tetradifon, tetramethrin, tetramethrin (1R-isomer), tetrasul, theta-cypermethrin, thiacloprid, thiamethoxam, thiapronil, thiatriphos, thiocyclam hydrogen oxalate, thiodicarb, thiofanox, thiometon, thiosultap-sodium, thuringiensin, tolfenpyrad, tralocythrin, tralomethrin, transfluthrin, triarathene, triazamate, triazophos, triazuron, trichlophenidine, trichlorfon, triflumuron, trimethacarb, vamidothion, vaniliprole, verbutin, *Verticillium lecanii*, WL-108477, WL-40027, YI-5201, YI-5301, YI-5302, XMC, xylylcarb, ZA-3274, zeta-cypermethrin, zolaprofos, ZXI-8901, the compound 3-methylphenyl propylcarbamate (tsumacide Z), the compound 3-(5-chloro-3-pyridinyl)-8-(2,2,2-trifluoroethyl)-8-azabicyclo[3.2.1]octane-3-carbonitrile (CAS-Reg. No. 185982-80-3) and the corresponding 3-endo-isomer (CAS-Reg. No. 185984-60-5) (cf. WO-96/37494, WO-98/25923), and also preparations which comprise insecticidally active plant extracts, nematodes, fungi or viruses.

A mixture with other known active compounds, such as herbicides, or with fertilizers and growth regulators, safeners or semiochemicals, is also possible.

In addition, the compounds of the formula (I) according to the invention also have very good antimycotic activity. They have a very broad antimycotic activity spectrum in particular against dermatophytes and yeasts, molds and diphasic fungi (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and *audouinii*. The list of these fungi by no means limits the mycotic spectrum covered, but is only for illustration.

The active compounds can be used as such, in the form of their formulations or the use forms prepared therefrom, such as ready-to-use solutions, suspensions, wettable powders, pastes, soluble powders, dusts and granules. Application is carried out in a customary manner, for example by watering, spraying, atomizing, broadcasting, dusting, foaming, spreading, etc. It is furthermore possible to apply the active compounds by the ultra-low-volume method, or to inject the active compound preparation or the active compound itself into the soil. It is also possible to treat the seeds of the plants.

When using the active compounds according to the invention as fungicides, the application rates can be varied within a relatively wide range, depending on the kind of application. For the treatment of parts of plants, the active compound application rates are generally between 0.1 and 10 000 g/ha, preferably between 10 and 1000 g/ha. For seed dressing, the active compound application rates are generally between 0.001 and 50 g per kilogram of seed, preferably between 0.01 and 10 g per kilogram of seed. For the treatment of the soil, the active compound application rates are generally between 0.1 and 10 000 g/ha, preferably between 1 and 5000 g/ha.

As already mentioned above, it is possible to treat all plants or their parts in accordance with the invention. In a preferred embodiment, wild plant species or plant varieties and plant cultivars which have been obtained by traditional biological breeding methods, such as hybridization or protoplast fusion, and the parts of these varieties and cultivars are treated. In a further preferred embodiment, transgenic plants and plant cultivars which have been obtained by recombinant methods, if appropriate in combination with conventional methods (genetically modified organisms), and their parts are treated. The term "parts" or "parts of plants" or "plant parts" has been explained above.

Plants which are treated particularly preferably in accordance with the invention are those of the plant cultivars which are in each case commercially available or in use. Plant cultivars are understood as meaning plants with new traits which have been bred either by conventional breeding, by mutagenesis or by recombinant DNA techniques. They may take the form of cultivars, biotypes and genotypes.

Depending on the plant species or plant cultivars, their location and growth conditions (soils, climate, vegetation period, nutrition), the treatment according to the invention may also result in superadditive ("synergistic") effects. Thus, for example, reduced application rates and/or a widened activity spectrum and/or an increase in the activity of the substances and compositions which can be used in accordance with the invention, better plant growth, increased tolerance to high or low temperatures, increased tolerance to drought or to salinity in the water or soil, increased flowering performance, facilitated harvesting, accelerated maturation, higher yields, higher quality and/or better nutritional value of the harvested products, better storage characteristics and/or processability of the harvested products are possible which exceed the effects which were actually to be expected.

The preferred transgenic plants or plant cultivars (those obtained by recombinant methods) to be treated in accordance with the invention include all those plants which, owing to the process of recombinant modification, were given genetic material which confers particular, advantageous, valuable traits to these plants. Examples of such properties are better plant growth, increased tolerance to high or low temperatures, increased tolerance to drought or to salinity in the water or soil, increased flowering performance, facilitated harvesting, accelerated maturation, higher yields, higher quality and/or higher nutritional value of the harvested products, better storage characteristics and/or better processability of the harvested products. Further examples of such traits, examples which must be mentioned especially, are better defense of the plants against animal and microbial pests, such as against insects, mites, phytopathogenic fungi, bacteria and/or viruses and an increased tolerance of the plants to certain herbicidal active compounds. Examples of transgenic plants which may be mentioned are the important crop plants, such as cereals (wheat, rice), corn, soybeans, potatoes, cotton, tobacco, oilseed rape and fruit plants (with the fruits apples, pears, citrus fruits and grapes), with particular emphasis on corn, soybeans, potatoes, cotton, tobacco, and oilseed rape. Traits which are especially emphasized are the increased defense of the plants against insects, arachnids, nematodes, and slugs and snails owing to toxins being formed in the plants, in particular toxins which are generated in the plants by the genetic material of *Bacillus thuringiensis* (for example by the genes CryIA(a), CryIA(b), CryIA(c), CryIIA, CryIIIA, CryIIIB2, Cry9c Cry2Ab, Cry3Bb and CryIF and their combinations; hereinbelow "Bt plants"). Other traits which are particularly emphasized are the increased defense of plants against fungi, bacteria and viruses by the systemic acquired resistance (SAR), systemin, phytoalexins, elicitors and resistance genes and correspondingly expressed proteins and toxins. Other traits which are especially emphasized are the increased tolerance of the plants to certain herbicidal active compounds, for example imidazolinones, sulfonylureas, glyphosate or phosphinotricin (for example "PAT" gene). The genes which confer the desired traits in each case may also be present in the transgenic plants in combination with one another. Examples of "Bt plants" which may be mentioned are corn cultivars, cotton cultivars, soybean cultivars and potato cultivars which are commercially available under the trade names YIELD GARD® (for example corn, cotton, soybean), KnockOut® (for example corn), StarLink® (for example corn), Bollgard® (cotton), Nucoton® (cotton) and NewLeaf® (potato). Examples of herbicide-tolerant plants which may be mentioned are corn cultivars, cotton cultivars and soybean cultivars which are commercially available under the trade names Roundup Ready® (tolerance to glyphosate, for example corn, cotton, soybean), Liberty Link®

(tolerance to phosphinotricin, for example oilseed rape), IMI® (tolerance to imidazolinones) and STS® (tolerance to sulfonylureas, for example corn). Herbicide-resistant plants (plants bred in a conventional manner for herbicide tolerance) which may be mentioned include also the varieties commercially available under the name Clearfield® (for example corn). Naturally, these statements also apply to plant cultivars having these genetic traits or genetic traits still to be developed, which plant cultivars will be developed and/or marketed in the future.

The plants listed can be treated particularly advantageously according to the invention with the compounds of the general formula (I) or the active compound mixtures according to the invention. The preferred ranges stated above for the active compounds and mixtures also apply to the treatment of these plants. Particular emphasis may be given to the treatment of plants with the compounds or mixtures specifically mentioned in the present text.

The preparation and the use of the active compounds according to the invention is illustrated in the examples below.

PREPARATION EXAMPLES

Example 1

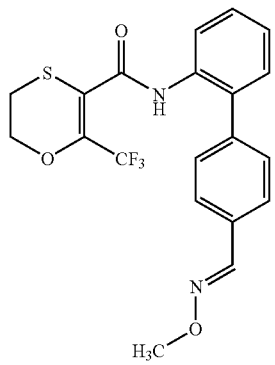

Process a)

A mixture of 6 ml of dichloromethane, 100 mg (0.467 mmol) of 6-trifluoromethyl-2,3-di-hydro-1,4-oxathiin-5-carboxylic acid, 88 mg (0.389 mmol) of 2'-aminobiphenyl-4-carbaldehyde O-methyl oxime, 100.6 mg (0.778 mmol) of N,N-diisopropylethylamine and 272 mg (0.584 mmol) of bromotripyrrolidinophosphonium hexafluorophosphate is stirred at room temperature for 2 days. 10 ml of water are then added to the reaction mixture and the organic phase is separated off and washed first with 10 ml of saturated ammonium chloride solution and then with 10 ml of water, dried over sodium sulfate and evaporated. The crude product is purified by preparative HPLC (reversed-phase silica gel ($C_{18}$), mobile phase: water/acetonitrile 34:66).

This gives: 35 mg (21% of theory) of N-[4'-(methoxyiminomethyl)-biphenyl-2-yl]-6-trifluoromethyl-2,3-dihydro-1,4-oxathiin-5-carboxamide of logP (pH 2.3)=3.51.

Example 2

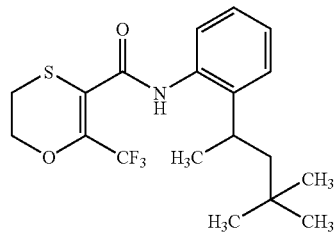

Process a)

300 mg (1.7 mmol) of 6-trifluoromethyl-2,3-dihydro-1,4-oxathiin-5-carbonyl chloride and 220 mg (1.1 mmol) of 2-(1,3,3-trimethylbutyl)phenylamine in 5 ml of acetonitrile are stirred in a closed vessel at room temperature for 4 days. 10 ml of water are then added to the reaction mixture and the organic phase is separated off and washed initially with 10 ml of saturated ammonium chloride solution and then with 10 ml of water, dried over sodium sulfate and evaporated. The crude product is purified by preparative HPLC (reversed-phase silica gel ($C_{18}$), mobile phase: 2% strength acetic acid/acetonitrile 25:75).

This gives: 200 mg (37% of theory) of N-[2-(1,3,3-trimethylbutyl)phenyl]-6-trifluoromethyl-2,3-dihydro-1,4-oxathiin-5-carboxamide of logP (pH 2.3)=4.18.

The compounds of the formula (I) listed in table 1 below were also obtained analogously to Examples 1 and 2 and in accordance with what was stated in the general description of the preparation processes (a) to (h) according to the invention:

TABLE 1

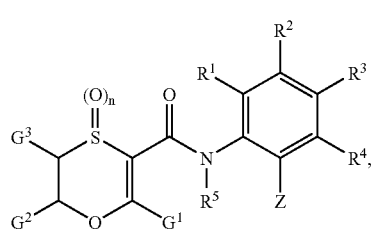

(I)

| No. | Z | $R^4$ | $R^3$ | $R^2$ | $R^1$ | $R^5$ | n | $G^2$ | $G^3$ | $G^1$ | logP m.p. |
|---|---|---|---|---|---|---|---|---|---|---|---|
| 3 | 1,3-dimethylbutyl | H | H | H | H | H | 0 | H | $CH_3$ | $CF_3$ | 4.24 |
| 4 | 1,3,3-trimethylbutyl | H | H | H | H | H | 0 | H | $CH_3$ | $CF_3$ | 4.53 |
| 5 | 4-fluoro-3-methylphenyl | H | H | H | H | H | 0 | H | $CH_3$ | $CF_3$ | 3.98 |

TABLE 1-continued

Structure (I): A 1,4-oxathiane ring bearing G1, G2, G3 substituents, with sulfur having (O)n, connected via a carboxamide C(=O)N(R5) to a phenyl ring substituted with R1, R2, R3, R4, and Z.

| No. | Z | R4 | R3 | R2 | R1 | R5 | n | G2 | G3 | G1 | logP m.p. |
|---|---|---|---|---|---|---|---|---|---|---|---|
| 6 | 3,4-dichlorophenyl | H | H | H | H | H | 0 | H | CH₃ | CF₃ | 4.26 |
| 7 | 4-chloro-3-trifluoro-methylphenyl | H | H | H | H | H | 0 | H | CH₃ | CF₃ | 4.30 |
| 8 | 4-isopropoximinomethyl-phenyl | H | H | H | H | H | 0 | H | CH₃ | CF₃ | 4.57 |
| 9 | 4-trifluoromethylphenyl | H | H | H | H | H | 0 | H | CH₃ | CF₃ | 4.06 |
| 10 | cycloheptyl | H | H | H | H | H | 0 | H | H | CF₃ | 137° C. |
| 11 | cyclopentyl | H | H | H | H | H | 0 | H | H | CF₃ | 159° C. |
| 12 | —CH(CH₃)—CH₂—C(CH₃)₂— | | H | H | H | H | 0 | H | H | CF₃ | 165° C. |
| 13 | cyclohexyl | H | F | H | H | H | 0 | H | H | CF₃ | 204-205° C. |
| 14 | cyclohexyl | H | Cl | H | H | H | 0 | H | H | CF₃ | 169-171° C. |
| 15 | bicyclo[2.2.1]hept-2-yl | H | H | H | H | H | 0 | H | H | CF₃ | 149° C. |
| 16 | cyclooctyl | H | H | H | H | H | 0 | H | H | CF₃ | 102° C. |
| 17 | 3,4-dichlorophenyl | H | F | H | H | H | 0 | H | H | CF₃ | 3.95 |
| 18 | 1,3-dimethylbutyl | H | H | H | H | H | 0 | H | H | CF₃ | 3.92 |
| 19 | 3,4-dichlorophenyl | H | H | H | H | H | 0 | H | H | CF₃ | 3.91 |
| 20 | 4-trifluoromethylphenyl | H | H | H | H | H | 0 | H | H | CF₃ | 3.73 |
| 21 | 4-isopropoximinomethyl-phenyl | H | H | H | H | H | 0 | H | H | CF₃ | 4.22 |
| 22 | 4-propoxyiminomethyl | H | H | H | H | H | 0 | H | H | CF₃ | 4.25 |
| 23 | 4-chloro-3-fluorophenyl | H | H | H | H | H | 0 | H | H | CF₃ | 3.62 |
| 24 | 3-chloro-4-fluorophenyl | H | H | H | H | H | 0 | H | H | CF₃ | 3.60 |
| 25 | 3-fluoro-4-propoxyimino-methylphenyl | H | H | H | H | H | 0 | H | H | CF₃ | 4.42 |
| 26 | 4-chloro-2-methylphenyl | H | H | H | H | H | 0 | H | H | CF₃ | 4.00 |
| 27 | 4-bromophenyl | H | H | H | H | H | 0 | H | H | CF₃ | 3.70 |
| 28 | cyclohexyl | H | H | H | H | H | 0 | H | H | CF₃ | 3.69 |
| 29 | 3-fluoro-4-trifluoromethyl-phenyl | H | H | H | H | H | 0 | H | H | CF₃ | 3.75 114-116° C. |
| 30 | 4-chloro-3-trifluoro-methylphenyl | H | H | H | H | H | 0 | H | H | CF₃ | 4.03 |
| 31 | (2-cyclohexyl)-1-methylethyl | H | H | H | H | H | 0 | H | H | CF₃ | 4.71 |
| 32 | 3,5-difluorophenyl | H | H | H | H | H | 0 | H | H | CF₃ | 3.35 167° C. |
| 33 | 4-iodophenyl | H | H | H | H | H | 0 | H | H | CF₃ | 3.85 |
| 34 | 1-methyl-3-butenyl | H | H | H | H | H | 0 | H | H | CF₃ | 3.33 |
| 35 | 4-fluoro-3-methylphenyl | H | H | H | H | H | 0 | H | H | CF₃ | 3.65 |
| 36 | 3-fluoro-4-methylphenyl | H | H | H | H | H | 0 | H | H | CF₃ | 3.62 |
| 37 | (2-cyclopentyl)-1-methylethyl | H | H | H | H | H | 0 | H | H | CF₃ | 4.38 |
| 38 | 3-chloro-4-methylphenyl | H | H | H | H | H | 0 | H | H | CF₃ | 3.89 |
| 39 | 1-methylbutyl | H | H | H | H | H | 0 | H | H | CF₃ | 3.63 |
| 40 | 4-(1-(3-propynyloxy-imino)ethyl)phenyl | H | H | H | H | H | 0 | H | H | CF₃ | 3.76 125-127° C. |
| 41 | 4-(1-amino-1-methoxy-iminomethyl)phenyl | H | H | H | H | H | 0 | H | H | CF₃ | 1.96 |
| 42 | 1-methylnonyl | H | H | H | H | H | 0 | H | H | CF₃ | 5.48 |
| 43 | 4-bromo-2-fluorophenyl | H | H | H | H | H | 0 | H | H | CF₃ | 3.57 |
| 44 | 3-chloro-5-fluorophenyl | H | H | H | H | H | 0 | H | H | CF₃ | 3.60 |
| 45 | 3-chloro-4-(1-methoxy-iminoethyl)phenyl | H | H | H | H | H | 0 | H | H | CF₃ | 3.45 |
| 46 | 3-fluoro-4-(1-methoxy-iminoethyl)phenyl | H | H | H | H | H | 0 | H | H | CF₃ | 3.69 |
| 47 | bicyclo[2.2.1]hept-2-yl | H | H | H | H | H | 0 | H | H | CF₃ | 4.32 |
| 48 | 1-methylhexyl | H | H | H | H | H | 0 | H | H | CF₃ | 4.34 |
| 49 | 1-cyclohexylethyl | H | H | H | H | H | 0 | H | H | CF₃ | 4.31 |
| 50 | 1,3-dimethylbutyl | H | F | H | H | H | 0 | H | H | CF₃ | 3.94 |
| 51 | 1-ethylpropyl | H | H | H | H | H | 0 | H | H | CF₃ | 3.62 |
| 52 | 1-methylbutyl | H | F | H | H | H | 0 | H | H | CF₃ | 3.67 |
| 53 | 3-chloro-4-trifluoro-methylphenyl | H | H | H | H | H | 0 | H | H | CF₃ | 3.98 100-102° C. |
| 54 | 1,3-dimethylpentyl | H | H | H | H | H | 0 | H | H | CF₃ | 4.25 |
| 55 | 2-(2,2-dichlorocyclo-propyl)-1-methylethyl | H | H | H | H | H | 0 | H | H | CF₃ | 3.92 |
| 56 | 4-(1-methoxyimino-propyl)phenyl | H | H | H | H | H | 0 | H | H | CF₃ | 4.08 |

TABLE 1-continued (I)

| No. | Z | R⁴ | R³ | R² | R¹ | R⁵ | n | G² | G³ | G¹ | logP m.p. |
|---|---|---|---|---|---|---|---|---|---|---|---|
| 57 | 4-bromo-3-fluorophenyl | H | H | H | H | H | 0 | H | H | CF₃ | 3.69 |
| 58 | 1,3,3-trimethylpentyl | H | H | H | H | H | 0 | H | H | CF₃ | 4.48 |
| 59 | bicyclo[2.2.1]hept-2-yl | H | H | H | H | H | 0 | CH₃ | H | CF₃ | 5.36 |
| 60 | —CH(CH₃)—CH₂—C(CH₃)₂— | | H | H | H | H | 0 | H | H | CF₃ | 4.18 |
| 61 | 4-trifluoromethylphenyl | H | H | H | H | H | 0 | CH₃ | H | CF₃ | 4.08 |
| 62 | 4-methoxyiminomethyl-phenyl | H | H | H | H | H | 0 | CH₃ | H | CF₃ | 3.81 |
| 63 | 1,3-dimethylbutyl | H | H | H | H | H | 0 | CH₃ | H | CF₃ | 4.27 |
| 64 | 4-isopropoximinomethyl-phenyl | H | H | H | H | H | 0 | CH₃ | H | CF₃ | 4.56 |
| 65 | 3,4-dichlorophenyl | H | H | H | H | H | 0 | CH₃ | H | CF₃ | 4.27 |
| 66 | 1,3,3-trimethylbutyl | H | H | H | H | H | 0 | CH₃ | H | CF₃ | 4.51 |
| 67 | 3,4-dichlorophenyl | H | F | H | H | H | 0 | CH₃ | H | CF₃ | 4.32 |
| 68 | 3-fluoro-4-propoxyimino-methylphenyl | H | H | H | H | H | 0 | CH₃ | H | CF₃ | 4.77 |
| 69 | 3-fluoro-4-methylphenyl | H | H | H | H | H | 0 | CH₃ | H | CF₃ | 3.99 |
| 70 | 4-fluoro-3-methylphenyl | H | H | H | H | H | 0 | CH₃ | H | CF₃ | 3.99 |
| 71 | 3-fluoro-4-trifluoromethyl-phenyl | H | H | H | H | H | 0 | CH₃ | H | CF₃ | 4.08 |
| 72 | 2-chloro-4-methoxyiminophenyl | H | H | H | H | H | 0 | H | H | CF₃ | 3.81 |
| 73 | 3,5-difluorophenyl | H | F | H | H | H | 0 | H | H | CF₃ | 3.49 |
| 74 | 3,5-difluorophenyl | H | H | H | F | H | 0 | H | H | CF₃ | 3.20 |
| 75 | 3,5-difluorophenyl | H | H | F | H | H | 0 | H | H | CF₃ | 3.70 |
| 76 | n-hexyl | H | H | H | H | H | 0 | H | H | CF₃ | 4.25 |
| 77 | 1-ethylbutyl | H | H | H | H | H | 0 | H | H | CF₃ | 4.07 |
| 78 | 4-cyanophenyl | H | H | H | H | H | 0 | H | H | CF₃ | 2.87 |
| 79 | 2,4-dichlorophenyl | H | H | H | H | H | 0 | H | H | CF₃ | 3.82 |
| 80 | 3,4-dichlorophenyl | H | H | H | H | H | 0 | H | H | cyclo-propyl | 3.53 |
| 81 | 1,3,3-trimethylbutyl | H | H | H | H | H | 0 | H | H | CHF₂ | 4.29 |
| 82 | 1,3-dimethylbutyl | H | H | H | H | H | 0 | H | H | CHF₂ | 4.03 |
| 83 | —CH(CH₃)—CH₂—C(CH₃)₂— | | H | H | H | H | 0 | H | H | CHF₂ | 4.00 |
| 84 | 3,4-dichlorophenyl | H | H | H | H | H | 0 | H | H | CHF₂ | 3.92 |
| 85 | 3-fluoro-4-propoxyimino-methylphenyl | H | H | H | H | H | 0 | H | H | CHF₂ | 4.52 |
| 86 | 4-methoxyiminomethyl-phenyl | H | H | H | H | H | 0 | H | H | CHF₂ | |
| 87 | 3-methyl-1-propylbutyl | H | H | H | H | H | 0 | H | H | CF₃ | 4.65 |
| 88 | 3-methyl-1-ethylbutyl | H | H | H | H | H | 0 | H | H | CF₃ | 4.30 |
| 89 | 1,3-dimethyl-1-butenyl | H | H | H | H | H | 0 | H | H | CF₃ | 4.32 |
| 90 | 1,3-dimethylbutyl | H | H | H | H | H | 2 | H | H | CF₃ | 3.53 |
| 91 | 4-bromophenyl | H | H | H | H | H | 2 | H | H | CF₃ | 3.35 |
| 92 | 4-chloro-2-methylphenyl | H | H | H | H | H | 2 | H | H | CF₃ | 3.66 |
| 93 | 3,4-dichlorophenyl | H | H | H | H | H | 2 | H | H | CF₃ | 3.57 |
| 94 | 1,2-dimethylbutyl | H | H | H | H | H | 0 | H | H | CF₃ | 3.88 |
| 95 | 4-chloro-3-fluorophenyl | H | H | H | H | H | 2 | H | H | CF₃ | 3.28 |
| 96 | (2-cyclopropyl)-1-methylethyl | H | H | H | H | H | 0 | H | H | CF₃ | 3.72 |
| 97 | 3,3-dimethyl-1-butynyl | H | H | H | H | H | 0 | H | H | CF₃ | 4.42 |
| 98 | 4-bromo-3-methylphenyl | H | H | H | H | H | 0 | H | H | CF₃ | 4.06 |
| 99 | 1,3-dimethylbutyl | H | H | H | H | —COCH₃ | 0 | H | H | CF₃ | 4.56 |
| 100 | 4-(2,2,2-trifluoro-N-meth-oxyethaneimidoyl)phenyl | H | H | H | H | H | 0 | H | H | CF₃ | 2.53 |
| 101 | 2,2-dichloro-1-methyl-cyclopropyl | H | H | H | H | H | 0 | H | H | CF₃ | 3.66 |
| 102 | 3-methylbutyl | H | H | H | H | H | 0 | H | H | CF₃ | 3.72 |
| 103 | 3,3-dimethylbutyl | H | H | H | H | H | 0 | H | H | CF₃ | 3.98 |

Preparation of the Precursors of the Formula (II)

Example (II-1)

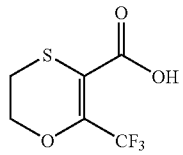

First step (II-1a):

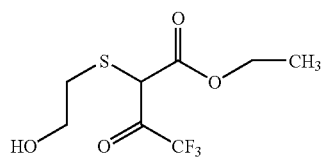

At about 5° C., 10.17 g (0.09 mol) of triethylamine are added dropwise to a solution of 20.0 g (0.092 mol) of ethyl 2-chloro-3-keto-4,4,4-trifluorobutyrate in 100 ml of toluene. A solution of 7.0 g (0.09 mol) of 2-mercaptoethanol in 5 ml of toluene is then added dropwise over a period of 1 hour, and the mixture is stirred at about 5° C. for another 2 hours. The suspension is filtered off, and the filter cake is washed with a little toluene. The filtrate is washed initially with 50 ml of 1N hydrochloric acid, then twice with 50 ml of saturated sodium bicarbonate solution and finally with 50 ml of water, dried over magnesium sulfate and concentrated.

This gives: 18.8 g (62% of theory) of ethyl 4,4,4-trifluoro-2-(2-hydroxyethylsulfanyl)-3-oxobutyrate (cf. Heterocycles, 1998, 48, 2253-2262).

Second Step (II-1b)

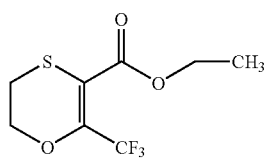

6.25 g (0.079 mol) of pyridine and then, dropwise over a period of 30 minutes and at 20° C., 4 g (0.079 mol) of thionyl chloride are added to a solution of 18.7 g (0.071 mol) of ethyl 4,4,4-trifluoro-2-(2-hydroxyethylsulfanyl)-3-oxobutyrate (II-1a) in 60 ml of toluene. Owing to the exothermic reaction, the temperature of the reaction mixture has to be cooled with ice-water. After the vigorous reaction has ended, the mixture is stirred at room temperature for another 5 hours. The mixture is filtered and the residue is washed with 10 ml of toluene. At about 10° C., 10.9 g (0.108 mol) of triethylamine are added dropwise over a period of 1 hour to the filtrate, and the mixture is stirred at room temperature for 16 hours. The reaction mixture is washed initially twice with 50 ml of 1N hydrochloric acid, then twice with 50 ml of saturated sodium bicarbonate solution and finally with 50 ml of water, dried over magnesium sulfate and concentrated. The residue is chromatographed on silica gel using petroleum ether/ethyl acetate (10:1 to 1:1).

This gives 12.6 g (59.4% of theory) of ethyl 6-trifluoromethyl-2,3-dihydro-1,4-oxathiin-5-carboxylate (cf. Heterocycles 1998, 48, 2253-2262).

Third Step:

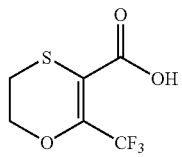

12.6 g (0.05 mol) of ethyl 6-trifluoromethyl-2,3-dihydro-1,4-oxathiin-5-carboxylate (II-1b) and 3.14 g (0.08 mol) of sodium hydroxide in 50 ml of water are boiled under reflux for 1 hour. The reaction mixture is cooled and extracted twice with dichloromethane. The aqueous phase is acidified to pH 2 using 6N hydrochloric acid and then extracted 5 times with diethyl ether. The combined organic extracts are dried over sodium sulfate and concentrated.

This gives: 9.2 g (82% of theory) of 6-trifluoromethyl-2,3-dihydro-1,4-oxathiin-5-carboxylic acid.

The compounds of the formula (II) mentioned below were also obtained analogously to Example (II-1):

Example (II-2)

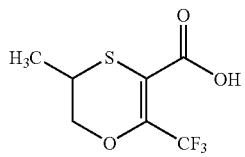

HPLC: logP=1.69

This compound is novel and also forms part of the subject-matter of the present application.

Example (II-3)

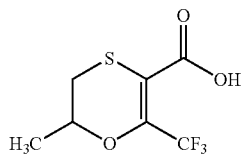

HPLC: logP=1.72

This compound is novel and also forms part of the subject-matter of the present application.

Example (II-4)

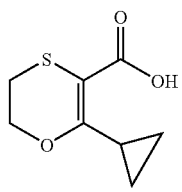

This compound is novel and also forms part of the subject-matter of the present application.

Example (II-5)

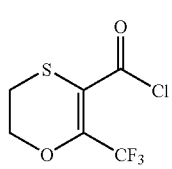

4.5 g (21 mmol) of 6-trifluoromethyl-2,3-dihydro-1,4-oxathiin-5-carboxylic acid (II-1) and 21 g of thionyl chloride in 10 ml of toluene are stirred at 80° C. for 4 hours. The end of the reaction is determined by regularly taking samples from the reaction solution, which samples are then mixed with methanol and used to prepare thin-layer chromatograms. After the reaction has ended, volatile components are distilled off. Three times, the residue is stirred with in each case 20 ml of dichloromethane and re-concentrated.

This gives 4.5 g (80% of theory) of 6-trifluoromethyl-2,3-dihydro-1,4-oxathiin-5-carbonyl chloride. The product was characterized by boiling a sample thereof with methanol for 2 hours and detecting the methyl 6-trifluoromethyl-2,3-dihydro-1,4-oxathiin-5-carboxylate obtained in this manner by GC/MS.

Preparation of the Precursors of the Formula (III)

Example (III-1)

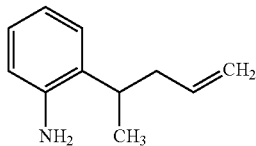

First Step III-1a)

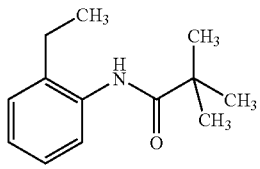

At 0° C., the 15 g (124 mmol) of pivaloyl chloride are added dropwise to a solution of 15 g (124 mmol) of 2-ethylaniline and 25 g (248 mmol) of triethylamine in 150 ml of dichloromethane, and the mixture is then stirred at 0° C. for 2 hours and subsequently without further cooling for 16 hours. The mixture is diluted with dichloromethane and washed initially with water and then with ammonium chloride solution, and the organic phase is separated off, dried over sodium sulfate and concentrated.

This gives 25 g (98% of theory) of N-(2-ethylphenyl)-2,2-dimethylpropionamide.

Second Step (III-1b)

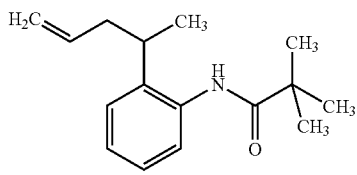

Under argon and at −25° C., initially 3.7 g (0.03 mol) of diazabicyclo[2.2.2]octane (DABCO) and then 44.5 ml (0.058 mol) of a solution of sec-butyllithium (1.3 M in hexane) are added to a solution of 5.6 g (0.0275 mol) of N-(2-ethylphenyl)-2,2-dimethylpropionamide (III-1a) in 150 ml of n-pentane/methyl t-butyl ether (1:1), and the mixture is then stirred at the same temperature for a further 2 hours. The mixture is then cooled to −78° C., 3.33 g (0.0275 mol) of allyl bromide are added dropwise and the mixture is stirred at −60 to −78° C. for 60 minutes. Residual sec-butyllithium is destroyed by addition of 30 ml of methanol. The mixture is warmed to room temperature and shaken with 50 ml of 5% strength phosphoric acid. The organic phase is separated off, filtered through silica gel and purified by preparative HPLC (reversed-phase silica gel ($C_{18}$), mobile phase: water/acetonitrile 38:62).

This gives 1.8 g (26% of theory) of 2,2-dimethyl-N-[2-(1-methylbut-3-enyl)phenyl]-propionamide.

Third Step (III-1)

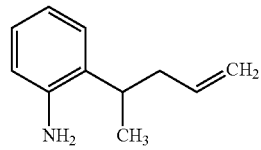

1.5 g (6.1 mmol) of 2,2-dimethyl-N-[2-(1-methylbut-3-enyl)phenyl]propionamide (III-1b) and 1.2 g (12.2 mmol) of concentrated hydrochloric acid in 24.5 ml of dioxane are stirred at 80° C. for 12 hours. 10 ml of water are added to the reaction mixture, which is then made alkaline with dilute aqueous sodium hydroxide solution and extracted 5 times with ethyl acetate. The combined organic extracts are dried over sodium sulfate and concentrated, filtered through silica gel (ethyl acetate/methanol 5:1) and purified by preparative HPLC (reversed-phase silica gel ($C_{18}$), mobile phase: 2% strength acetic acid/acetonitrile 70:30).

This gives 0.3 g (30% of theory) of 2-(1-methylbut-3-enyl)phenylamine.

The compounds of the formula (III) mentioned below were also obtained analogously to Example (III-1):

Example (III-2)

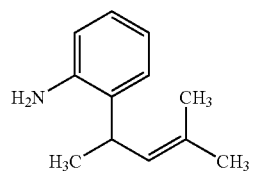

HPLC: logP=1.19

This compound is novel and also forms part of the subject-matter of the present application.

Example (III-3)

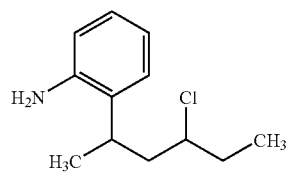

HPLC: logP=2.3

2-(3-Chloro-1-methylpentyl)phenylamine (III-3) is obtained by initially preparing N-[2-(2-cyclopropylisopropyl)phenyl]-2,2-dimethylpropanamide analogously to Examples (III-1a) and (III-1b). In the third step, the material is reacted with hydrochloric acid which gives, in addition to 2-(2-cyclopropylisopropyl)phenylamine, also the compound (III-3).

Example (III-4)

First Step (III-4a)

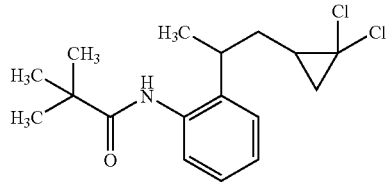

At room temperature, 100 mg of benzyltriethylammonium chloride and 1 ml of 50% strength aqueous sodium hydroxide solution are added successively to a solution of 900 mg (3.7 mmol) of 2,2-dimethyl-N-[2-(1-methylbut-3-enyl)phenyl] propionamide (III-1b) in 5 ml of chloroform/water (1:1), and the mixture is stirred for 5 days. The reaction mixture is diluted further with 20 ml of chloroform and washed with 50 ml of sodium chloride solution, and the organic phase is separated off, dried over sodium sulfate and concentrated.

This gives 800 mg (37% of theory) of N-{2-[2-(2,2-dichlorocyclopropyl)-1-methylethyl]-phenyl}-2,2-dimethylpropionamide of logP (pH 2.3)=3.77.

This compound is novel and also forms part of the subject-matter of the present invention.

Second Step (III-4b)

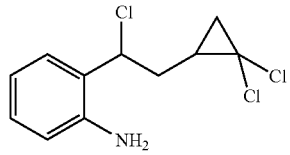

800 mg (1.34 mmol) of N-{2-[2-(2,2-dichlorocyclopropyl)-1-methylethyl]phenyl}-2,2-dimethylpropionamide (III-4a) are dissolved in 25 ml of dioxane, 0.1 ml of concentrated hydrochloric acid is added and the mixture is stirred at room temperature for 72 hours and at 80° C. for 24 hours. The mixture is diluted with ice-water, made alkaline with concentrated aqueous sodium hydroxide solution and extracted with 50 ml of ethyl acetate. The organic phase is dried over sodium sulfate and concentrated under reduced pressure. Using methanol, the residue is filtered through silica gel and purified by preparative HPLC (reversed-phase silica gel ($C_{18}$), mobile phase: 2% strength phosphoric acid/acetonitrile 52:48).

This gives 0.8 g (60% of theory) of 2-[2-(2,2-dichlorocyclopropyl)-1-methylethyl]-phenylamine of logP (pH 2.3)=2.52.

This compound is novel and also forms part of the subject-matter of the present application.

The given logP values were determined in accordance with EEC Directive 79/831 Annex V.A8 by HPLC (High Performance Liquid Chromatography) on a reversed-phase column (C 18). Temperature: 43° C.

Mobile phases for the determination in the acidic range (pH 2.3): 0.1% aqueous phosphoric acid, acetonitrile; linear gradient from 10% acetonitrile to 90% acetonitrile.

Calibration was carried out using unbranched alkan-2-ones (having 3 to 16 carbon atoms) with known logP values (determination of the logP values by the retention times using linear interpolation between two successive alkanones).

The lambda max values were determined in the maxima of the chromatographic signals using the UV spectra from 200 nm to 400 nm.

USE EXAMPLES

Example A

*Venturia* Test (Apple)/Protective

Solvents: 24.5 parts by weight of acetone 24.5 parts by weight of dimethylacetamide Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, the plants are inoculated with an aqueous conidia suspension of the apple scab pathogen *Venturia inaequalis* and then remain in an incubation cabin at about 20° C. and 100% relative atmospheric humidity for 1 day.

The plants are then placed in a greenhouse at about 21° C. and a relative atmospheric humidity of about 90%.

Evaluation is carried out 10 days after the inoculation. 0% means an efficacy which corresponds to that of the control, whereas an efficacy of 100% means that no infection is observed.

Active compounds, application rates and test results are shown in the table below.

TABLE A

*Venturia* test (apple)/protective

| Ex. | Active compound | Application rate of active compound in g/ha | % efficacy |
|---|---|---|---|
| 12 | (structure) | 100 | 100 |
| 17 | (structure) | 100 | 100 |

TABLE A-continued

Venturia test (apple)/protective

| Ex. | Active compound | Application rate of active compound in g/ha | % efficacy |
|---|---|---|---|
| 20 | 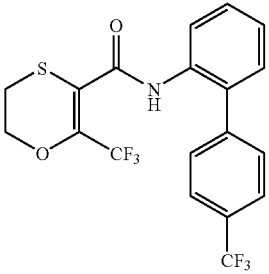 | 100 | 88 |
| 18 | 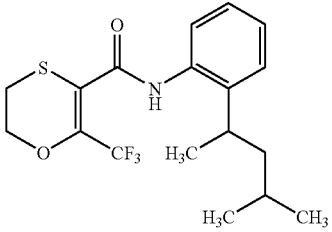 | 100 | 100 |
| 19 | 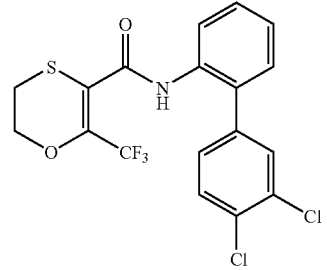 | 100 | 100 |
| 21 | 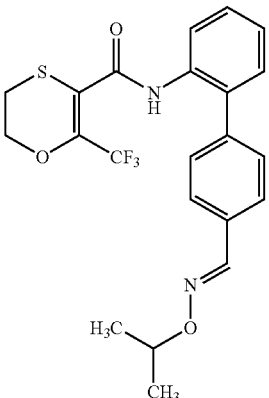 | 100 | 100 |
| 22 | 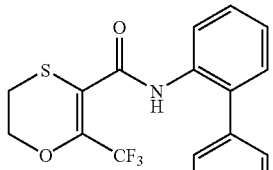 | 100 | 100 |
| 2 | 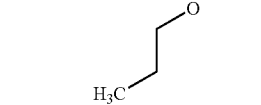 | 100 | 98 |

Example B

Botrytis Test (Bean)/Protective

Solvents: 24.5 parts by weight of acetone 24.5 parts by weight of dimethylacetamide Emulsifier: 1 part by weight of alkylaryl polyglycol ether To produce a suitable preparation of active compound, 1 part by weight of active compound is mixed with the stated amounts of solvents and emulsifier, and the concentrate is diluted with water to the desired concentration.

To test for protective activity, young plants are sprayed with the preparation of active compound at the stated application rate. After the spray coating has dried on, 2 small pieces of agar colonized with Botrytis cinerea are placed onto each leaf. The inoculated plants are placed in a dark chamber at about 20° C. and 100% relative atmospheric humidity.

2 days after the inoculation, the size of the infected areas on the leaves is evaluated. 0% means an efficacy which corresponds to that of the control, whereas an efficacy of 100% means that no infection is observed.

Active compounds, application rates and test results are shown in the table below.

TABLE B

Botrytis test (bean)/protective

| Ex. | Active compound | Application rate of active compound in g/ha | % efficacy |
|---|---|---|---|
| 12 | (structure) | 500 | 97 |
| 17 | (structure) | 500 | 96 |
| 20 | (structure) | 500 | 100 |
| 18 | (structure) | 500 | 100 |
| 19 | (structure) | 500 | 100 |
| 21 | (structure) | 500 | 100 |
| 22 | (structure) | 500 | 100 |
| 2 | (structure) | 500 | 100 |

Example C

*Alternaria* Test (Tomato)/Protective

Solvent: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application rate. 1 day after the treatment, the plants are inoculated with a spore suspension of *Alternaria solani* and are then allowed to stand at 100% relative humidity and 20°

C. for 24 h. The plants are then allowed to stand at 96% relative atmospheric humidity and a temperature of 20° C.

Evaluation is carried out 7 days after the inoculation. 0% means an efficacy which corresponds to that of the control, whereas an efficacy of 100% means that no infection is observed.

Active compounds, application rates and test results are shown in the table below.

TABLE C

| | | *Alternaria* test (tomato)/protective | |
|---|---|---|---|
| Ex. | Active compound | Application rate of active compound in g/ha | % efficacy |
| 26 | 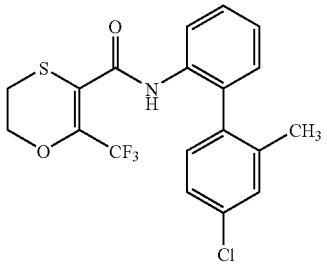 | 750 | 100 |
| 2 | 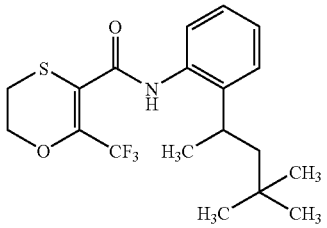 | 750 | 100 |
| 19 | 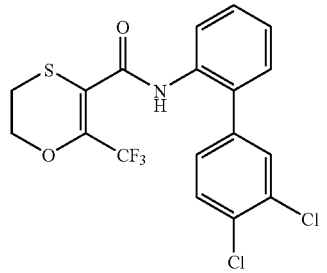 | 750 | 100 |

TABLE C-continued

| | | *Alternaria* test (tomato)/protective | |
|---|---|---|---|
| Ex. | Active compound | Application rate of active compound in g/ha | % efficacy |
| 21 | 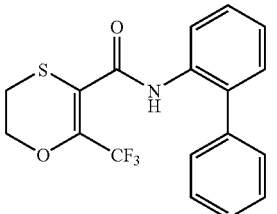 | 750 | 100 |

Example D

*Puccinia* Test (Wheat)/Protective
Solvent: N,N-dimethylacetamide
Emulsifier: alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are sprayed with a conidia suspension of *Puccinia* recondite. The plants remain in an incubation cabin at 20° C. and 100% relative atmospheric humidity for 48 h.

The plants are then placed in a greenhouse at a temperature of about 20° C. and a relative atmospheric humidity of 80% to promote the development of rust pustules.

Evaluation is carried out 10 days after the inoculation. 0% means an efficacy which corresponds to that of the control, whereas an efficacy of 100% means that no infection is observed.

Active compounds, application rates, amounts of solvent, amounts of emulsifier and test results are shown in the table below.

TABLE D

| | | *Puccinia* test (wheat)/protective | | |
|---|---|---|---|---|
| Ex. | Active compound | Application rate of active compound in g/ha | % efficacy | Parts by weight of solvent/emulsifier |
| 18 | 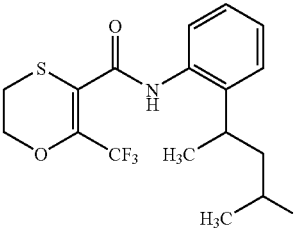 | 500 | 100 | 25/0.5 |

TABLE D-continued

*Puccinia* test (wheat)/protective

| Ex. | Active compound | Application rate of active compound in g/ha | % efficacy | Parts by weight of solvent/ emulsifier |
|---|---|---|---|---|
| 17 | (structure) | 500 | 86 | 25/0.6 |
| 35 | (structure) | 500 | 88 | 25/0.6 |
| 19 | (structure) | 500 | 100 | 25/0.6 |
| 2 | (structure) | 500 | 100 | 25/0.6 |
| 24 | (structure) | 500 | 100 | 25/0.6 |

TABLE D-continued

Puccinia test (wheat)/protective

| Ex. | Active compound | Application rate of active compound in g/ha | % efficacy | Parts by weight of solvent/ emulsifier |
|---|---|---|---|---|
| 38 | (structure) | 500 | 88 | 25/0.6 |
| 37 | (structure) | 500 | 93 | 25/0.6 |
| 39 | (structure) | 500 | 100 | 25/0.6 |
| 56 | (structure) | 500 | 88 | 25/0.6 |
| 57 | (structure) | 500 | 88 | 25/0.6 |

TABLE D-continued

*Puccinia* test (wheat)/protective

| Ex. | Active compound | Application rate of active compound in g/ha | % efficacy | Parts by weight of solvent/ emulsifier |
|---|---|---|---|---|
| 54 | (structure) | 500 | 100 | 50/1.0 |
| 29 | (structure) | 500 | 94 | 50/1.0 |
| 53 | (structure) | 500 | 100 | 50/1.0 |
| 79 | (structure) | 500 | 86 | 50/1.0 |
| 23 | (structure) | 500 | 89 | 50/1.0 |

TABLE D-continued

Puccinia test (wheat)/protective

| Ex. | Active compound | Application rate of active compound in g/ha | % efficacy | Parts by weight of solvent/ emulsifier |
|---|---|---|---|---|
| 27 | 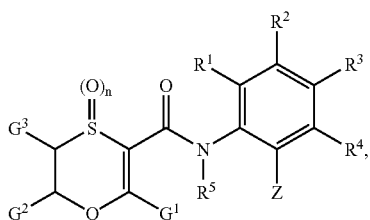 | 500 | 88 | 50/1.0 |
| 82 | | 500 | 100 | 50/1.0 |

The invention claimed is:

1. An oxathiincarboxamide of formula (I)

(I)

in which
G¹ represents halogen, trifluoromethyl, difluoromethyl, or cyclopropyl,
G² and G³ independently of one another represent hydrogen or methyl,
n represents 0, 1 or 2,
R¹, R², R³, and R⁴ independently of one another represent hydrogen, fluorine, chlorine, methyl, isopropyl, or methylthio,
R⁵ represents hydrogen, $C_1$-$C_8$-alkyl, —COR⁶, or —CONR⁷R⁸,
R⁶ represents hydrogen, $C_1$-$C_8$-alkyl, $C_1$-$C_8$-alkoxy, $C_1$-$C_4$-alkoxy-$C_1$-$C_4$-alkyl, or $C_3$-$C_8$-cycloalkyl; represents $C_1$-$C_6$-haloalkyl, $C_1$-$C_6$-haloalkoxy, halo-$C_1$-$C_4$-alkoxy-$C_1$-$C_4$-alkyl, or $C_3$-$C_8$-halocycloalkyl having in each case 1 to 9 fluorine, chlorine, and/or bromine atoms; or represents —COR¹¹,
R⁷ and R⁸ independently of one another represent hydrogen, $C_1$-$C_8$-alkyl, $C_1$-$C_4$-alkoxy-$C_1$-$C_4$-alkyl, or $C_3$-$C_8$-cycloalkyl; represent $C_1$-$C_8$-haloalkyl, halo-$C_1$-$C_4$-alkoxy-$C_1$-$C_4$-alkyl, or $C_3$-$C_8$-halocycloalkyl having in each case 1 to 9 fluorine, chlorine, and/or bromine atoms; or R⁷ and R⁸ together with the nitrogen atom to which they are attached form a saturated heterocycle having 5 to 8 ring atoms, where the heterocycle is optionally mono- or polysubstituted by identical or different substituents selected from the group consisting of halogen and $C_1$-$C_4$-alkyl,
R¹¹ represents hydrogen, $C_1$-$C_8$-alkyl, $C_1$-$C_8$-alkoxy, $C_1$-$C_4$-alkoxy-$C_1$-$C_4$-alkyl, or $C_3$-$C_8$-cycloalkyl; represents $C_1$-$C_6$-haloalkyl, $C_1$-$C_6$-haloalkoxy, halo-$C_1$-$C_4$-alkoxy-$C_1$-$C_4$-alkyl, or $C_3$-$C_8$-halocycloalkyl having in each case 1 to 9 fluorine, chlorine, and/or bromine atoms, and
Z represents Z³, where
Z³ represents unsubstituted $C_5$-$C_{20}$-alkyl or represents $C_1$-$C_{20}$-alkyl that is mono- or polysubstituted by identical or different substituents selected from the group consisting of chlorine and $C_3$-$C_6$-cycloalkyl.

2. The oxathiincarboxamide of formula (I) as claimed in claim 1 in which
n represents 0 or 2.

3. The oxathiincarboxamide of formula (I) as claimed in claim 1 in which R⁵ represents hydrogen.

4. The oxathiincarboxamide of formula (I) as claimed in claim 1 in which
R¹ represents hydrogen, fluorine, chlorine, or methyl,
R² represents hydrogen, fluorine, chlorine, isopropyl, or methylthio,
R³ represents hydrogen, fluorine, chlorine, or methyl, and
R⁴ represents hydrogen, fluorine, chlorine, or methyl.

5. A composition for controlling unwanted microorganisms comprising one or more oxathiincarboxamides of formula (I) as claimed in claim 1 and one or more extenders and/or surfactants.

6. A hydroxyalkyloxathiincarboxamide of formula (VIII)

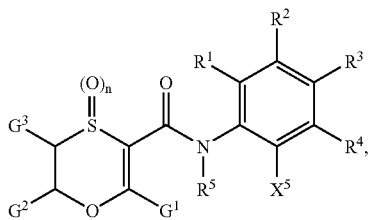

in which
- $G^1$ represents trifluoromethyl, difluoromethyl, or cyclopropyl,
- $G^2$ and $G^3$ independently of one another represent hydrogen or methyl,
- n represents 0, 1 or 2,
- $R^1$, $R^2$, $R^3$, and $R^4$ independently of one another represent hydrogen, fluorine, chlorine, methyl, isopropyl, or methylthio,
- $R^5$ represents hydrogen, $C_1$-$C_8$-alkyl, —$COR^6$, or —$CONR^7R^8$,
- $R^6$ represents hydrogen, $C_1$-$C_8$-alkyl, $C_1$-$C_8$-alkoxy, $C_1$-$C_4$-alkoxy-$C_1$-$C_4$-alkyl, or $C_3$-$C_8$-cycloalkyl; represents $C_1$-$C_6$-haloalkyl, $C_1$-$C_6$-haloalkoxy, halo-$C_1$-$C_4$-alkoxy-$C_1$-$C_4$-alkyl, or $C_3$-$C_8$-halocycloalkyl having in each case 1 to 9 fluorine, chlorine, and/or bromine atoms; or represents —$COR^{11}$,
- $R^7$ and $R^8$ independently of one another represent hydrogen, $C_1$-$C_8$-alkyl, $C_1$-$C_4$-alkoxy-$C_1$-$C_4$-alkyl, or $C_3$-$C_8$-cycloalkyl; represent $C_1$-$C_8$-haloalkyl, halo-$C_1$-$C_4$-alkoxy-$C_1$-$C_4$-alkyl, or $C_3$-$C_8$-halocycloalkyl having in each case 1 to 9 fluorine, chlorine, and/or bromine atoms; or $R^7$ and $R^8$ together with the nitrogen atom to which they are attached form a saturated heterocycle having 5 to 8 ring atoms, where the heterocycle is optionally mono- or polysubstituted by identical or different substituents selected from the group consisting of halogen and $C_1$-$C_4$-alkyl,
- $R^{11}$ represents hydrogen, $C_1$-$C_8$-alkyl, $C_1$-$C_8$-alkoxy, $C_1$-$C_4$-alkoxy-$C_1$-$C_4$-alkyl, or $C_3$-$C_8$-cycloalkyl; represents $C_1$-$C_6$-haloalkyl, $C_1$-$C_6$-haloalkoxy, halo-$C_1$-$C_4$-alkoxy-$C_1$-$C_4$-alkyl, or $C_3$-$C_8$-halocycloalkyl having in each case 1 to 9 fluorine, chlorine, and/or bromine atoms, and
- $X^5$ represents $C_2$-$C_{20}$-hydroxyalkyl that is optionally additionally mono- or polysubstituted by identical or different substituents selected from the group consisting of halogen and $C_3$-$C_6$-cycloalkyl.

* * * * *